(12) United States Patent
Kaula et al.

(10) Patent No.: US 9,507,912 B2
(45) Date of Patent: Nov. 29, 2016

(54) METHOD AND SYSTEM OF SIMULATING A PULSE GENERATOR ON A CLINICIAN PROGRAMMER

(71) Applicant: Greatbatch Ltd., Clarence, NY (US)

(72) Inventors: Norbert Kaula, Arvada, CO (US); Yohannes Iyassu, Denver, CO (US)

(73) Assignee: Nuvectra Corporation, Plano, TX (US)

( * ) Notice: Subject to any disclaimer, the term of this patent is extended or adjusted under 35 U.S.C. 154(b) by 159 days.

(21) Appl. No.: 14/015,107

(22) Filed: Aug. 30, 2013

(65) Prior Publication Data

US 2014/0068758 A1    Mar. 6, 2014

Related U.S. Application Data

(60) Provisional application No. 61/695,437, filed on Aug. 31, 2012.

(51) Int. Cl.
  *G06F 21/00* (2013.01)
  *G06F 19/00* (2011.01)
  *G06F 21/31* (2013.01)

(52) U.S. Cl.
  CPC ........... *G06F 19/34* (2013.01); *G06F 19/3406* (2013.01); *G06F 21/31* (2013.01); *G06F 2221/2149* (2013.01)

(58) Field of Classification Search
  CPC .... G06F 19/34; G06F 19/3406; G06F 21/31; G06F 2221/2149; A61N 1/37247
  USPC ............................................... 726/19; 715/71
  See application file for complete search history.

(56) References Cited

U.S. PATENT DOCUMENTS

| 4,432,360 A | 2/1984 | Mumford et al. |
| 5,286,202 A | 2/1994 | De Gyarfas et al. |
| 5,304,206 A | 4/1994 | Baker, Jr. et al. |

(Continued)

FOREIGN PATENT DOCUMENTS

| EP | 1192972 | 4/2002 |
| EP | 2277586 | 1/2011 |

(Continued)

OTHER PUBLICATIONS

Synalink Features, SynaMed Web Page, http://synamed.com/synalinkFeatures.html., Copyright 2010, 2 pgs.

(Continued)

*Primary Examiner* — John B King
(74) *Attorney, Agent, or Firm* — Haynes and Boone, LLP; Eric Li

(57) ABSTRACT

The present disclosure involves a method of simulating a pulse generator on a portable electronic device. A graphical user interface is provided via a touch-sensitive screen of the portable electronic device. The graphical user interface is configured to facilitate interactive user engagements with the portable electronic device. A pulse generator simulator is launched on the portable electronic device in response to a request from the user. The pulse generator simulator provides a virtual pulse generator that duplicates a plurality of functionalities and features of an actual pulse generator. The virtual pulse generator is programmed based on user input received via the graphical user interface. One or more statuses of the virtual pulse generator are then displayed via the graphical user interface.

24 Claims, 17 Drawing Sheets

(56) References Cited

U.S. PATENT DOCUMENTS

| | | |
|---|---|---|
| 5,312,446 A | 5/1994 | Holschbach et al. |
| 5,370,672 A | 12/1994 | Fowler et al. |
| 5,383,914 A | 1/1995 | O'Phelan |
| 5,421,830 A | 6/1995 | Epstein et al. |
| 5,628,776 A | 5/1997 | Paul et al. |
| 5,692,907 A * | 12/1997 | Glassel et al. ............ 434/262 |
| 5,713,937 A | 2/1998 | Nappholz et al. |
| 5,722,999 A | 3/1998 | Snell |
| 5,724,996 A | 3/1998 | Piunti |
| 5,819,740 A | 10/1998 | Muhlenberg |
| 5,879,374 A | 3/1999 | Powers et al. |
| 5,905,500 A | 5/1999 | Kamen et al. |
| 5,938,690 A | 8/1999 | Law et al. |
| 6,016,447 A | 1/2000 | Juran et al. |
| 6,016,448 A | 1/2000 | Busacker et al. |
| 6,052,624 A | 4/2000 | Mann |
| 6,083,156 A | 7/2000 | Lisiecki |
| 6,148,233 A | 11/2000 | Owen et al. |
| 6,154,675 A | 11/2000 | Juran et al. |
| 6,216,036 B1 | 4/2001 | Jenkins et al. |
| 6,246,414 B1 | 6/2001 | Kawasaki |
| 6,249,705 B1 | 6/2001 | Snell |
| 6,278,890 B1 | 8/2001 | Chassaing et al. |
| 6,307,554 B1 | 10/2001 | Arai et al. |
| 6,308,102 B1 | 10/2001 | Sieracki et al. |
| 6,327,549 B1 * | 12/2001 | Bingham et al. ............ 702/180 |
| 6,345,200 B1 | 2/2002 | Mouchawar et al. |
| 6,386,882 B1 | 5/2002 | Linberg |
| 6,442,432 B2 | 8/2002 | Lee |
| 6,525,727 B1 | 2/2003 | Junkins et al. |
| 6,564,104 B2 | 5/2003 | Nelson et al. |
| 6,587,104 B1 | 7/2003 | Hoppe |
| 6,611,267 B2 | 8/2003 | Migdal et al. |
| 6,622,048 B1 | 9/2003 | Mann et al. |
| 6,669,631 B2 | 12/2003 | Norris et al. |
| 6,786,405 B2 | 9/2004 | Weidenhoefer |
| 6,852,080 B2 | 2/2005 | Bardy |
| 6,882,982 B2 | 4/2005 | McMenimen et al. |
| 6,895,280 B2 | 5/2005 | Meadows et al. |
| 6,920,360 B2 | 7/2005 | Lee et al. |
| 6,931,155 B1 | 8/2005 | Gioia |
| 6,961,448 B2 | 11/2005 | Nichols et al. |
| 6,961,617 B1 | 11/2005 | Snell |
| 7,003,349 B1 | 2/2006 | Andersson et al. |
| 7,034,823 B2 | 4/2006 | Dunnett |
| 7,058,453 B2 | 6/2006 | Nelson et al. |
| 7,060,030 B2 | 6/2006 | Von Arx et al. |
| 7,065,409 B2 | 6/2006 | Mazar |
| 7,066,910 B2 | 6/2006 | Bauhahn et al. |
| 7,076,303 B2 | 7/2006 | Linberg |
| 7,087,015 B1 | 8/2006 | Comrie et al. |
| 7,092,761 B1 | 8/2006 | Cappa et al. |
| 7,107,102 B2 | 9/2006 | Daignault et al. |
| 7,142,923 B2 | 11/2006 | North et al. |
| 7,181,286 B2 | 2/2007 | Sieracki et al. |
| 7,181,505 B2 | 2/2007 | Haller et al. |
| 7,184,837 B2 | 2/2007 | Goetz |
| 7,239,926 B2 | 7/2007 | Goetz |
| 7,266,412 B2 | 9/2007 | Stypulkowski |
| 7,299,085 B2 | 11/2007 | Bergelson et al. |
| 7,359,751 B1 | 4/2008 | Erickson et al. |
| 7,373,204 B2 | 5/2008 | Gelfand et al. |
| 7,440,806 B1 | 10/2008 | Whitehurst et al. |
| 7,452,336 B2 | 11/2008 | Thompson |
| 7,463,927 B1 | 12/2008 | Chaouat |
| 7,474,223 B2 | 1/2009 | Nycz et al. |
| 7,481,759 B2 | 1/2009 | Whitehurst et al. |
| 7,489,970 B2 | 2/2009 | Lee et al. |
| 7,496,403 B2 | 2/2009 | Cao et al. |
| 7,499,048 B2 | 3/2009 | Sieracki et al. |
| 7,505,815 B2 | 3/2009 | Lee et al. |
| 7,551,960 B2 | 6/2009 | Forsberg et al. |
| 7,602,384 B2 | 10/2009 | Rosenberg et al. |
| 7,617,002 B2 | 11/2009 | Goetz |
| 7,627,372 B2 | 12/2009 | Vaisnys et al. |
| 7,640,059 B2 | 12/2009 | Forsberg et al. |
| 7,657,317 B2 | 2/2010 | Thacker et al. |
| 7,685,005 B2 | 3/2010 | Riff et al. |
| 7,711,603 B2 | 5/2010 | Vanker et al. |
| 7,720,549 B2 | 5/2010 | Schroeppel et al. |
| 7,747,330 B2 | 6/2010 | Nolan et al. |
| 7,774,067 B2 | 8/2010 | Keacher et al. |
| 7,778,710 B2 | 8/2010 | Propato |
| 7,801,596 B2 | 9/2010 | Fischell et al. |
| 7,801,611 B2 | 9/2010 | Persen et al. |
| 7,805,199 B2 | 9/2010 | KenKnight et al. |
| 7,822,483 B2 | 10/2010 | Stone et al. |
| 7,853,323 B2 | 12/2010 | Goetz |
| 7,885,712 B2 | 2/2011 | Goetz et al. |
| 7,890,180 B2 | 2/2011 | Quiles |
| 7,928,995 B2 | 4/2011 | Daignault |
| 7,934,508 B2 | 5/2011 | Behm |
| 7,940,933 B2 | 5/2011 | Corndorf |
| 7,953,492 B2 | 5/2011 | Corndorf |
| 7,953,612 B1 | 5/2011 | Palmese et al. |
| 7,957,808 B2 | 6/2011 | Dawant et al. |
| 7,978,062 B2 | 7/2011 | LaLonde et al. |
| 7,991,482 B2 | 8/2011 | Bradley |
| 8,014,863 B2 | 9/2011 | Zhang et al. |
| 8,021,298 B2 | 9/2011 | Baird et al. |
| 8,027,726 B2 | 9/2011 | Ternes |
| 8,046,241 B1 | 10/2011 | Dodson |
| 8,060,216 B2 | 11/2011 | Greenberg et al. |
| 8,068,915 B2 | 11/2011 | Lee et al. |
| 8,068,918 B2 | 11/2011 | Vallapureddy et al. |
| 8,078,440 B2 | 12/2011 | Otto et al. |
| 8,082,162 B2 | 12/2011 | Flood |
| 8,121,702 B2 | 2/2012 | King |
| 8,135,566 B2 | 3/2012 | Marshall et al. |
| 8,140,160 B2 | 3/2012 | Pless et al. |
| 8,140,167 B2 | 3/2012 | Donders et al. |
| 8,160,328 B2 | 4/2012 | Goetz et al. |
| 8,160,704 B2 | 4/2012 | Freeberg |
| 8,165,385 B2 | 4/2012 | Reeves et al. |
| 8,187,015 B2 | 5/2012 | Boyd et al. |
| 8,200,324 B2 | 6/2012 | Shen et al. |
| 8,200,340 B2 | 6/2012 | Skelton et al. |
| 8,219,206 B2 | 7/2012 | Skelton et al. |
| 8,233,991 B2 | 7/2012 | Woods et al. |
| 8,246,680 B2 | 8/2012 | Betz et al. |
| 8,249,713 B2 | 8/2012 | Fang et al. |
| 8,255,060 B2 | 8/2012 | Goetz et al. |
| 8,323,218 B2 | 12/2012 | Davis et al. |
| 8,326,433 B2 | 12/2012 | Blum et al. |
| 8,340,775 B1 | 12/2012 | Cullen et al. |
| 8,382,666 B1 | 2/2013 | Mao et al. |
| 8,386,032 B2 | 2/2013 | Bachinski et al. |
| 8,401,666 B2 | 3/2013 | Skelton et al. |
| 8,428,727 B2 | 4/2013 | Bolea et al. |
| 2001/0037220 A1 | 11/2001 | Merry et al. |
| 2003/0036783 A1 * | 2/2003 | Bauhahn ............ A61N 1/37247 607/59 |
| 2003/0076301 A1 | 4/2003 | Tsuk et al. |
| 2003/0107572 A1 | 6/2003 | Smith et al. |
| 2003/0139652 A1 | 7/2003 | Kang et al. |
| 2003/0171911 A1 | 9/2003 | Fairweather |
| 2003/0177031 A1 | 9/2003 | Malek |
| 2004/0088374 A1 | 5/2004 | Webb et al. |
| 2004/0122477 A1 | 6/2004 | Whitehurst et al. |
| 2004/0210273 A1 | 10/2004 | Wang |
| 2005/0107831 A1 | 5/2005 | Hill et al. |
| 2005/0149356 A1 | 7/2005 | Cyr et al. |
| 2005/0168460 A1 | 8/2005 | Razdan et al. |
| 2005/0277872 A1 | 12/2005 | Colby et al. |
| 2006/0089888 A1 | 4/2006 | Roger |
| 2006/0100832 A1 | 5/2006 | Bowman |
| 2006/0241720 A1 | 10/2006 | Woods et al. |
| 2006/0242159 A1 | 10/2006 | Bishop et al. |
| 2006/0282168 A1 | 12/2006 | Sherman et al. |
| 2007/0055318 A1 * | 3/2007 | Forsberg ............ A61N 1/08 607/31 |
| 2007/0078497 A1 | 4/2007 | Vandanacker |
| 2007/0093998 A1 | 4/2007 | El-Baroudi |
| 2007/0179349 A1 | 8/2007 | Hoyme et al. |

(56) References Cited

U.S. PATENT DOCUMENTS

| | | |
|---|---|---|
| 2007/0203537 A1 | 8/2007 | Goetz et al. |
| 2007/0203538 A1 | 8/2007 | Stone et al. |
| 2007/0203543 A1 | 8/2007 | Stone et al. |
| 2007/0213790 A1 | 9/2007 | Nolan et al. |
| 2008/0004675 A1 | 1/2008 | King et al. |
| 2008/0033303 A1 | 2/2008 | Wariar et al. |
| 2008/0046036 A1 | 2/2008 | King et al. |
| 2008/0140161 A1 | 6/2008 | Goetz et al. |
| 2008/0177362 A1 | 7/2008 | Phillips et al. |
| 2008/0218517 A1 | 9/2008 | Holmdahl |
| 2008/0262565 A1 | 10/2008 | Bentwich |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0089034 A1 | 4/2009 | Penney et al. |
| 2009/0099624 A1 | 4/2009 | Kokones et al. |
| 2009/0132009 A1 | 5/2009 | Torgerson et al. |
| 2009/0136094 A1 | 5/2009 | Driver et al. |
| 2009/0196471 A1 | 8/2009 | Goetz et al. |
| 2009/0228070 A1* | 9/2009 | Goetz et al. ............ 607/59 |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennett et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0224523 A1 | 9/2011 | Burdiman |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0192874 A1 | 8/2012 | Bolea et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Connor et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| WO | WO 9959106 | 11/1999 |
| WO | WO 0209808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Boston Scientific Corporation, "Boston Scientific Precision Spectra System Programming Manual", Copyright 2010, 580 pgs.

* cited by examiner

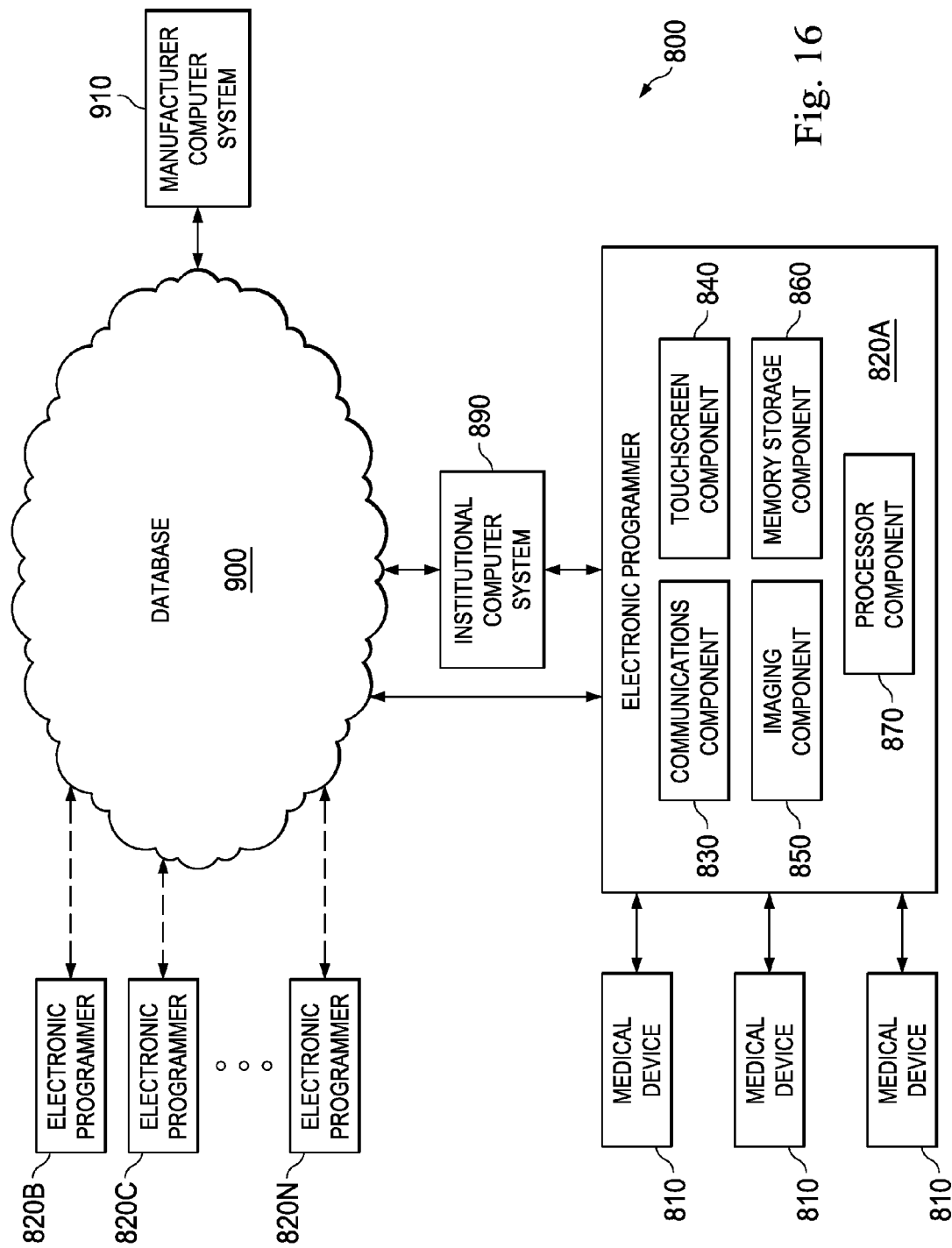

METHOD AND SYSTEM OF SIMULATING A PULSE GENERATOR ON A CLINICIAN PROGRAMMER

PRIORITY DATA

The present application is a utility application of provisional U.S. Patent Application No. 61/695,437, filed on Aug. 31, 2012, entitled "Method and System of Stimulating a Pulse Generator on a Clinician Programmer," the disclosure of which is hereby incorporated by reference in its entirety.

BACKGROUND

As medical device technologies continue to evolve, active implanted medical devices have gained increasing popularity in the medical field. For example, one type of implanted medical device includes neurostimulator devices, which are battery-powered or battery-less devices designed to deliver electrical stimulation to a patient. Through proper electrical stimulation, the neurostimulator devices can provide pain relief for patients or restore bodily functions.

Implanted medical devices (for example, a pulse generator) can be controlled using an electronic programming device such as a clinician programmer or a patient programmer. These programmers can be used by medical personnel or the patient to define the particular electrical stimulation therapy to be delivered to a target area of the patient's body, to alter one or more parameters of the electrical stimulation therapy, or otherwise to conduct communications with a patient.

Despite many advances made in the field of neurostimulation, one drawback is that the existing clinician programmers have not been able to provide a sufficiently versatile simulation of the pulse generator. Currently, a user who wishes to test the capabilities of a clinician programmer would have to establish a connection between the clinician programmer and an actual pulse generator. After the connection has been established, the user may use the clinician programmer to communicate with the pulse generator and verify that the communications produced the correct results. However, establishing an actual connection between a clinician programmer and a pulse generator is not always practical, for example in situations where a salesperson for the clinician programmer merely wants to demonstrate the features of the clinician programmer to a target audience. In addition, even if an actual connection between the clinician programmer and the pulse generator could be made, it is still time-consuming to do so, and it would be more convenient to simulate such connection. Unfortunately, existing clinician programmers lack the capability to provide a satisfactory simulation of an actual pulse generator.

Therefore, although existing clinician programmers have been generally adequate for their intended purposes, they have not been entirely satisfactory in every aspect.

SUMMARY

One aspect of the present disclosure involves an electronic apparatus for simulating a pulse generator. The electronic device includes: a touchscreen display configured to receive an input from a user and display an output; a memory storage component configured to store programming code; and a computer processor configured to execute the programming code to perform the following tasks: providing a graphical user interface via the touchscreen display of the portable electronic device; launching a pulse generator simulator on the portable electronic device in response to a request from the user, wherein the pulse generator simulator provides a virtual pulse generator that duplicates a plurality of functionalities and features of an actual pulse generator; programming the virtual pulse generator based on user input received via the graphical user interface; and displaying one or more statuses of the virtual pulse generator via the graphical user interface.

Another aspect of the present disclosure involves a medical system. The medical system includes: a pulse generator configured to generate electrical pulses for stimulating target nerve tissues of a patient; and a portable electronic device configured to simulate the pulse generator, wherein the portable electronic device includes a non-transitory, tangible machine-readable storage medium storing executable instructions that when executed electronically by one or more processors, perform the following steps: providing a graphical user interface via a touch-sensitive screen of the portable electronic device, the graphical user interface being configured to facilitate interactive user engagements with the portable electronic device; launching a pulse generator simulator on the portable electronic device in response to a request from the user, wherein the pulse generator simulator provides a virtual pulse generator that duplicates a plurality of functionalities and features of the pulse generator; programming the virtual pulse generator based on user input received via the graphical user interface; and displaying one or more statuses of the virtual pulse generator via the graphical user interface.

Yet another aspect of the present disclosure involves a method of simulating a pulse generator on a portable electronic device. The method includes: providing a graphical user interface via a touch-sensitive screen of the portable electronic device, the graphical user interface being configured to facilitate interactive user engagements with the portable electronic device; launching a pulse generator simulator on the portable electronic device in response to a request from the user, wherein the pulse generator simulator provides a virtual pulse generator that duplicates a plurality of functionalities and features of an actual pulse generator; programming the virtual pulse generator based on user input received via the graphical user interface; and displaying one or more statuses of the virtual pulse generator via the graphical user interface.

Yet one more aspect of the present disclosure involves and electronic apparatus for simulating a pulse generator. The electronic apparatus includes: user interface means for communicating with a user; memory storage means for storing executable programming instructions; and computer processor means for executing the programming instructions to perform the following steps: launching a pulse generator simulator in response to a request from the user, wherein the pulse generator simulator provides a virtual pulse generator that duplicates a plurality of functionalities and features of an actual pulse generator that is programmable to deliver electrical stimulation therapy for a patient; programming the virtual pulse generator based on user input received via the user interface means; and displaying one or more statuses of the virtual pulse generator via the user interface means.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIG. 16 is a simplified block diagram of a medical system/infrastructure according to various aspects of the present disclosure.

DETAILED DESCRIPTION

Figure 1:
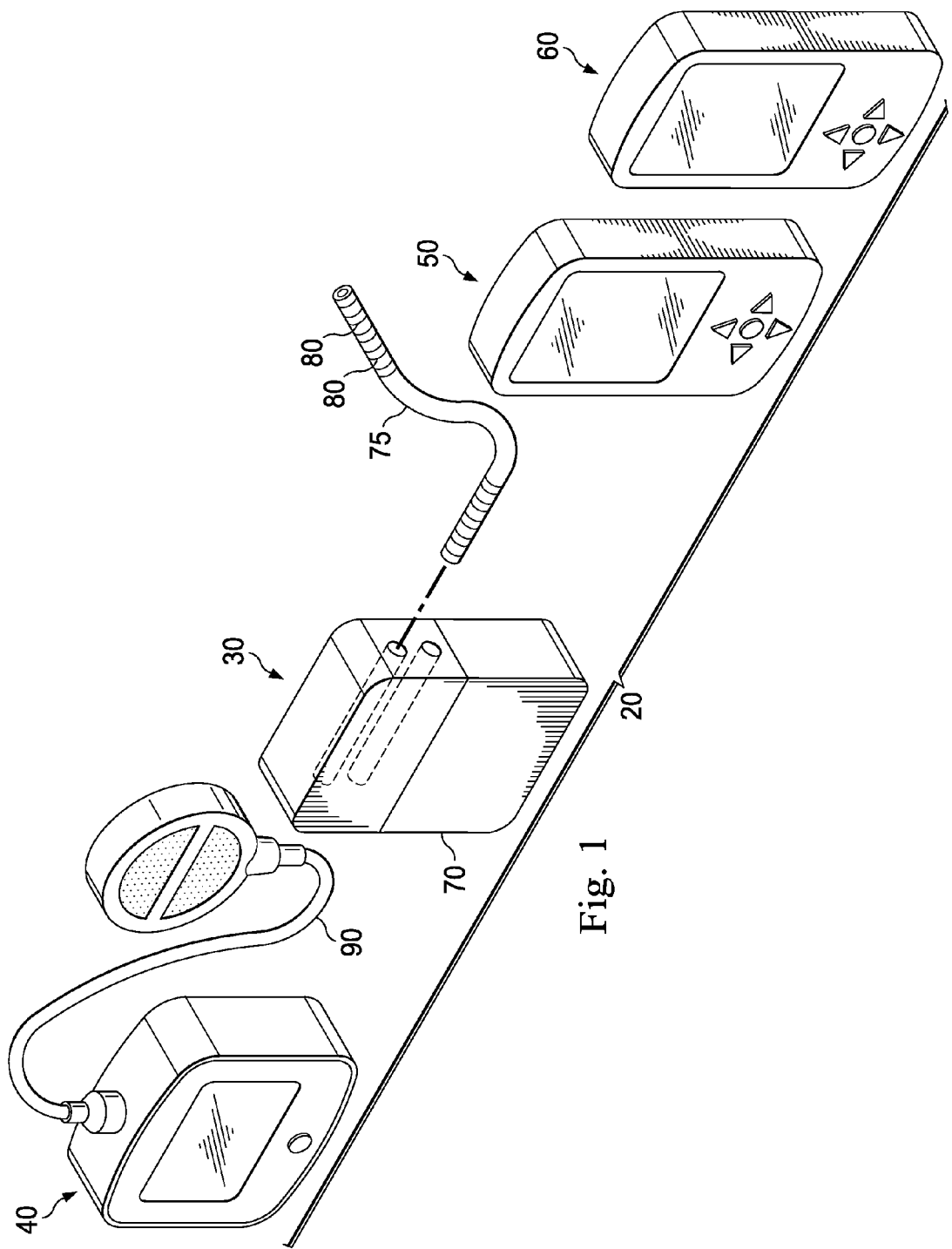
FIG. 1 is a simplified block diagram of an example medical environment in which evaluations of a patient may be conducted according to various aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

The use of active implanted medical devices has become increasingly prevalent over time. Some of these implanted medical devices include neurostimulator devices that are capable of providing pain relief by delivering electrical stimulation to a patient. In that regards, electronic programmers have been used to configure or program these neurostimulators (or other types of suitable active implanted medical devices) so that they can be operated in a certain manner. These electronic programmers include clinician programmers and patient programmers, each of which may be a handheld device. For example, a clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

In recent years, these electronic programmers have achieved significant improvements, for example, improvements in size, power consumption, lifetime, and ease of use. Despite these advances, the capabilities of electronic programmers have not been fully exploited, for example, in terms of providing a versatile simulation or emulation of a pulse generator (an example type of neurostimulator). In general, simulation or emulation refers to the use of computers to imitate or represent another device and the capabilities of that device. Currently, the electronic programmers lack the capability to fully simulate or emulate a pulse generator. Therefore, in order to test the functionalities or demonstrate the features of the electronic programmer, a connection between the electronic programmer and an actual pulse generator would have to be established. After the connection has been established, the user may use the electronic programmer to communicate with the pulse generator and verify that the communications produced the correct results.

However, establishing an actual connection between an electronic programmer and a pulse generator is not always practical. There are situations where a salesperson for the electronic programmer merely wants to demonstrate the features (e.g., features involving the programming of the pulse generator) of the electronic programmer to a target audience. In addition, even if a connection between the electronic programmer and an actual pulse generator could be made, it is still time-consuming to do so, and it would be more convenient to simulate such connection.

Therefore, the current lack of testing and demonstration capabilities has the following shortcomings:

There is no way to exercise and/or test how an electronic programmer will interact with a pulse generator without using a pulse generator that is connected to leads (electrodes that deliver electrical pulses from a pulse generator).

There is no way to demonstrate an electronic programmer's ability to communicate with a pulse generator without using a pulse generator.

To address the issues discussed above, the present disclosure offers a method and system of providing a versatile simulation or emulation of a pulse generator on an electronic device. In various embodiments, the electronic device may be a clinician programmer, a patient programmer, a tablet computer, or a computer, as discussed below in more detail.

FIG. 1 is a simplified block diagram of a medical device system 20 is illustrated to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end (referred to as a connection end) of one or more percutaneous, or skin-penetrating, leads. The other end (referred to as a stimulating end) of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer. However, it is understood that the electronic programmer may also be the patient programmer 50 or other touch screen programming devices (such as smart-phones or tablet computers) in other embodiments.

FIGS. 2-10 illustrate an example user interface 100 of a clinician programmer application according to some embodiments. The clinician programmer application may refer to software that is running on the clinician programmer (e.g., the clinician programmer 60 in FIG. 1) that allows user interaction therewith. For example, the user may use the clinician programmer application to program a pulse generator to generate electrical pulses that provide stimulation therapy (e.g., paresthesia) when delivered to a patient's target nerve tissues. In alternative embodiments, the clinician programmer application may be software that is running on a desktop computer, a laptop computer, or a portable electronic device such as a smartphone or a tablet computer. The user interface 100 is displayed on a touch-sensitive screen of the clinician programmer and allows for interactive engagement from a target user, which may be a healthcare professional, for example a doctor or a nurse. The user and the healthcare professional are interchangeably referred in the following paragraphs, but it is understood that they need not necessarily be the same entity. It is also understood that the engagement of the touch-sensitive screen does not require an actual touch. For example the screen may have proximity sensors that allow the clinician programmer to respond to a detected proximity of a user's finger or a stylus-like tool.

Figure 2:
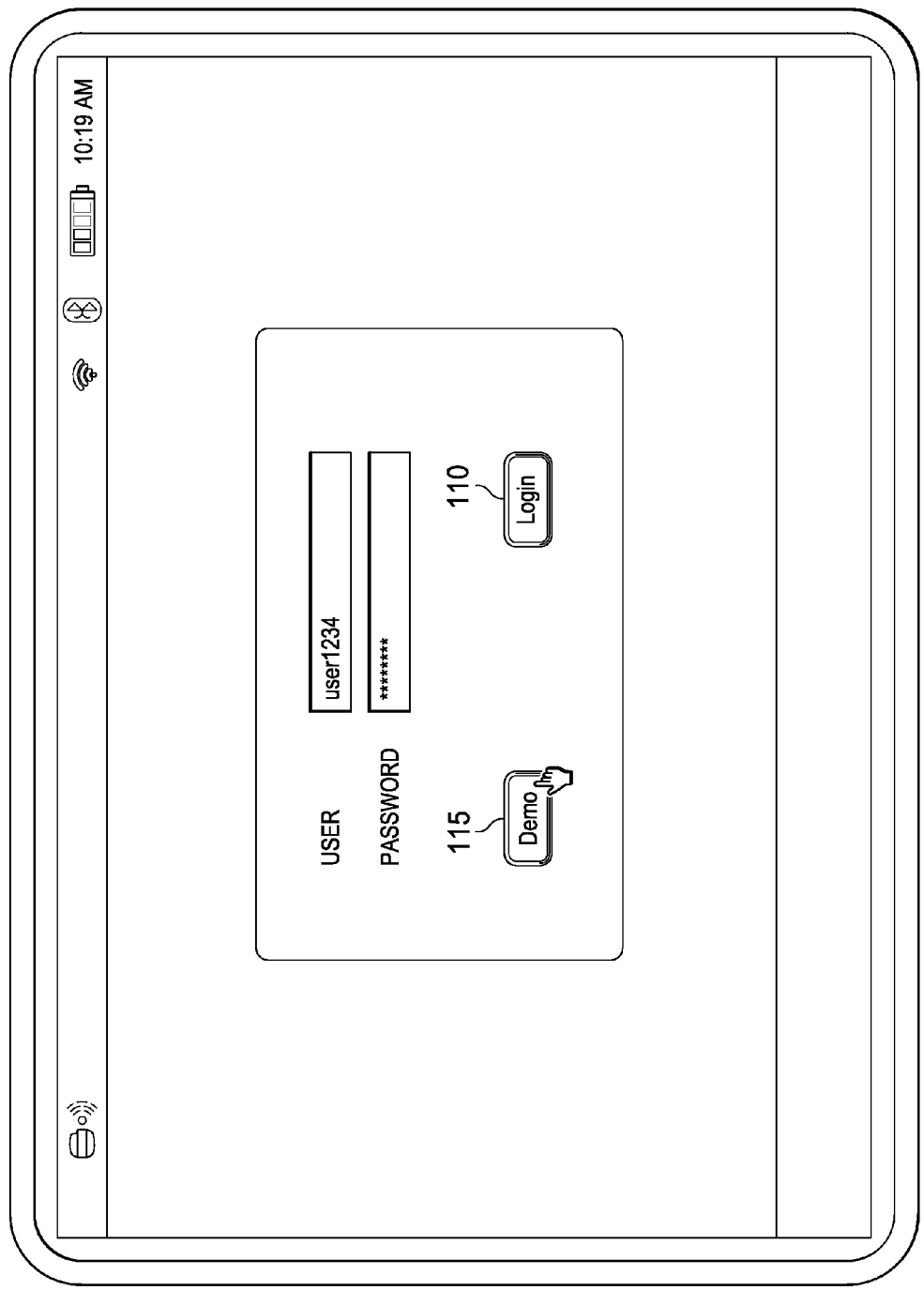
FIGS. 2-10 are different screens of a user interface for simulating a pulse generator according to various aspects of the present disclosure.

Referring to FIG. 2, the user interface 100 displays a login screen. The login screen may be invoked when the clinician programmer receives a request from a user to access the clinician programmer. For example, in some embodiments, the login screen may be invoked after the user powers on the clinician programmer. The login screen prompts the user to enter a username and a password. If the user does not enter a valid combination of the username and password, the user will not be able to access the clinician programmer at all. If the user is able to supply a correct combination of username and password, however, the login screen presents the user with two access options. One option is a normal login, which may be chosen by the user clicking on a button 110 (the "Login" virtual button displayed in FIG. 2). The normal login gives the user standard access to the clinician programmer, which may allow the user to program an actual pulse generator to deliver a stimulation therapy for a target patient, for example.

The other option is using the clinician programmer in a simulator mode, which is referred to as a demo mode in the illustrated embodiment but may also be referred to as a test mode or another suitable name in alternative embodiments. The simulator mode (interchangeably referred to as demo mode hereinafter) may be activated by the user clicking on a button 115 (the "Demo" virtual button displayed in FIG. 2). Among other things, the demo option allows the user to demonstrate the features and functionalities of the clinician programmer (e.g., features that otherwise would involve a connection to an actual pulse generator) without having to program an actual pulse generator or establishing a connection thereto. Rather, a pulse generator simulator application (also referred to as pulse generator simulator) is launched by entering the demo mode. The pulse generator simulator application runs as software on the hardware of the clinician programmer and simulates or emulates one or more aspects of a target actual pulse generator. In some embodiments, all the features and functionalities of the target pulse generator are simulated or emulated by the pulse generator simulator. The clinician programmer communicates with the pulse generator simulator to carry out programming of a virtual pulse generator, which does not physically exist but otherwise corresponds to an actual pulse generator. From the user's perspective, it is as if the clinician programmer is connected to a real pulse generator.

In some embodiments, the button 115 (the engagement of which gives the user access to the demo mode) may not be displayed until after the user has entered a correct combination of username and password. In other embodiments, the button 115 may be displayed but may not be selectable (e.g., it may be grayed out) until after the correct combination of username and password has been entered. In yet other embodiments, the button 115 may be displayed and may be selectable before the user enters the username and password. In any case, the separation of the button 115 from the button 110 (the engagement of which gives the user normal access to the clinician programmer) helps the user distinguish these options and prevents accidental or inadvertent user selections.

Figure 3:
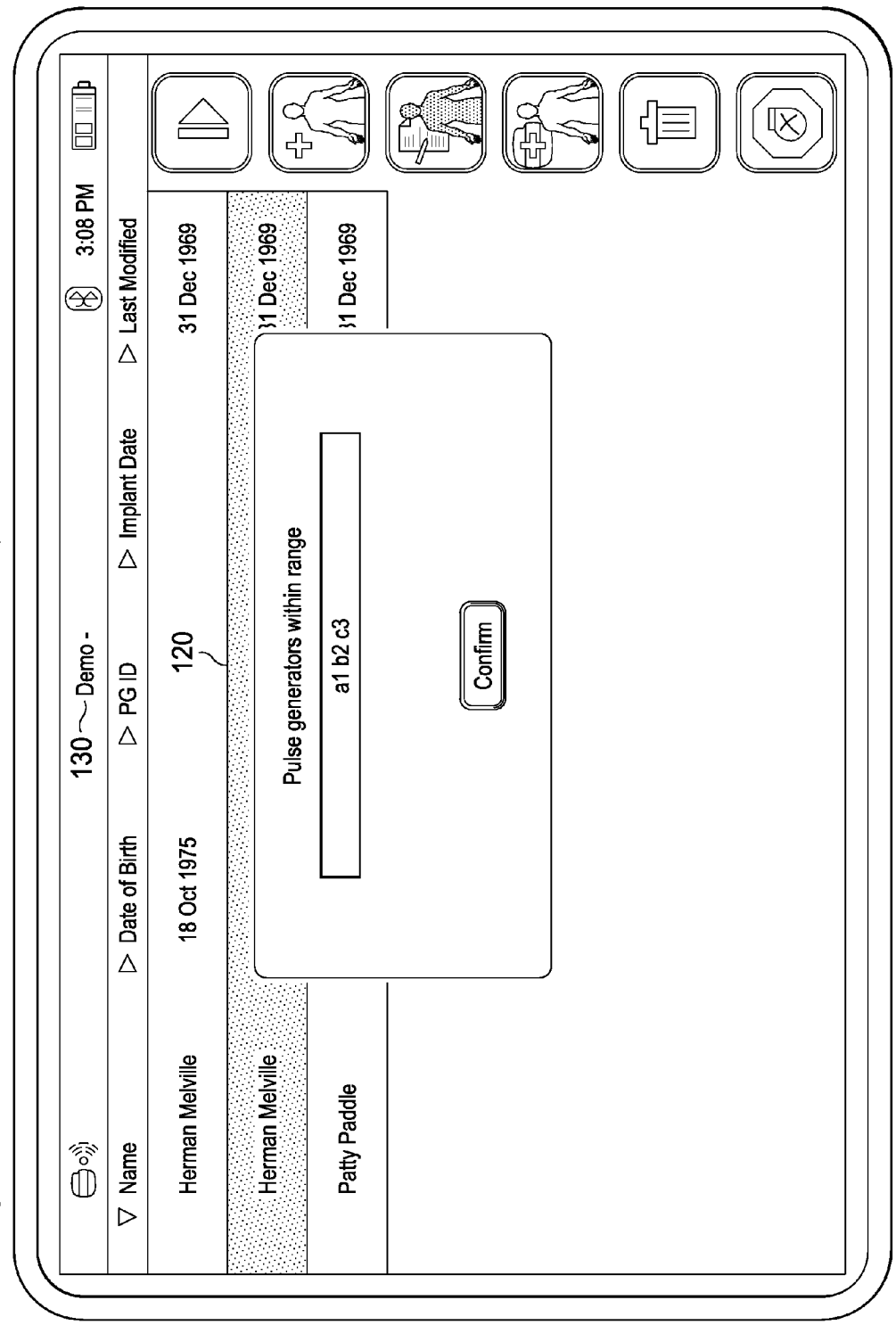

Referring now to FIG. 3, after the user clicks on the button 115 to enter the demo mode, the pulse generator simulator is launched. A discovery message 120 is displayed by the clinician programmer. As is the case with actual pulse generators, the "presence" of the virtual pulse generator provided by the pulse generator simulator may be "discovered" by the clinician programmer. The discovery message 120 notifies the user that the virtual pulse generator with an address "a1 b2 c3" is "discovered" by the clinician programmer as the pulse generator that is within communication range of the clinician programmer. To the user, the "discovery" of the virtual pulse generator appears the same as if the virtual pulse generator "a1 b2 c3" had been a real actual pulse generator nearby.

Figure 4:
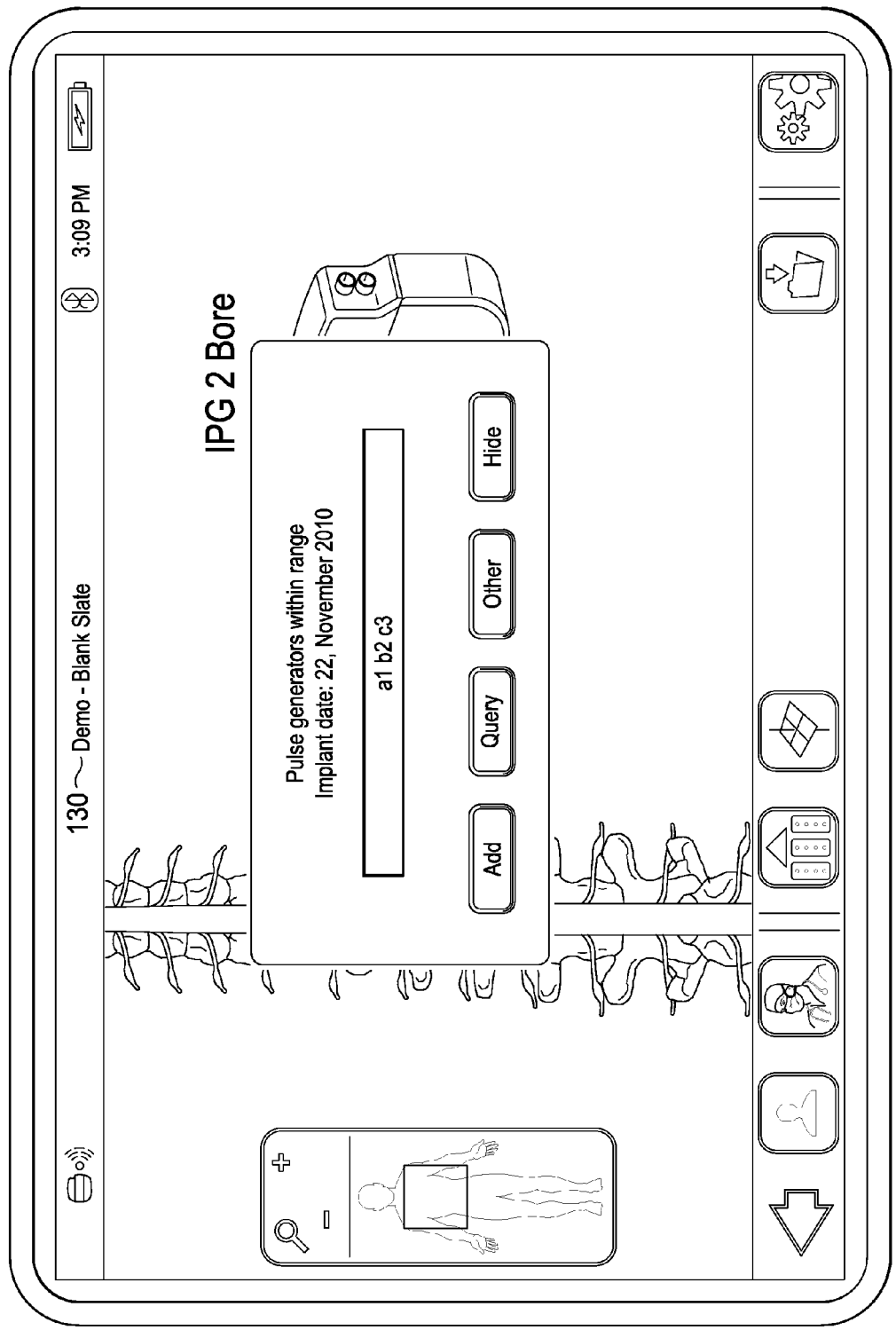

Though the "discovery" of the virtual pulse generator occurs in the patient selection stage/process of stimulation programming in the embodiment shown, it is understood that the virtual pulse generator may be discovered in a different stage/process of stimulation programming as well. For example, as shown in FIG. 4, the pulse generator simulator may allow a virtual pulse generator to be discovered at an implant selection screen. The user may add the virtual pulse generator (with the address "a1 b2 c3") to be added by clicking the "add" button. Again, from the user's perspective, the virtual pulse generator may as well be a real pulse generator, though the heading 130 (shown in FIGS. 3-4) still reminds the user that the pulse generator being engaged by the clinician programmer is still a virtual pulse generator.

Figure 5:
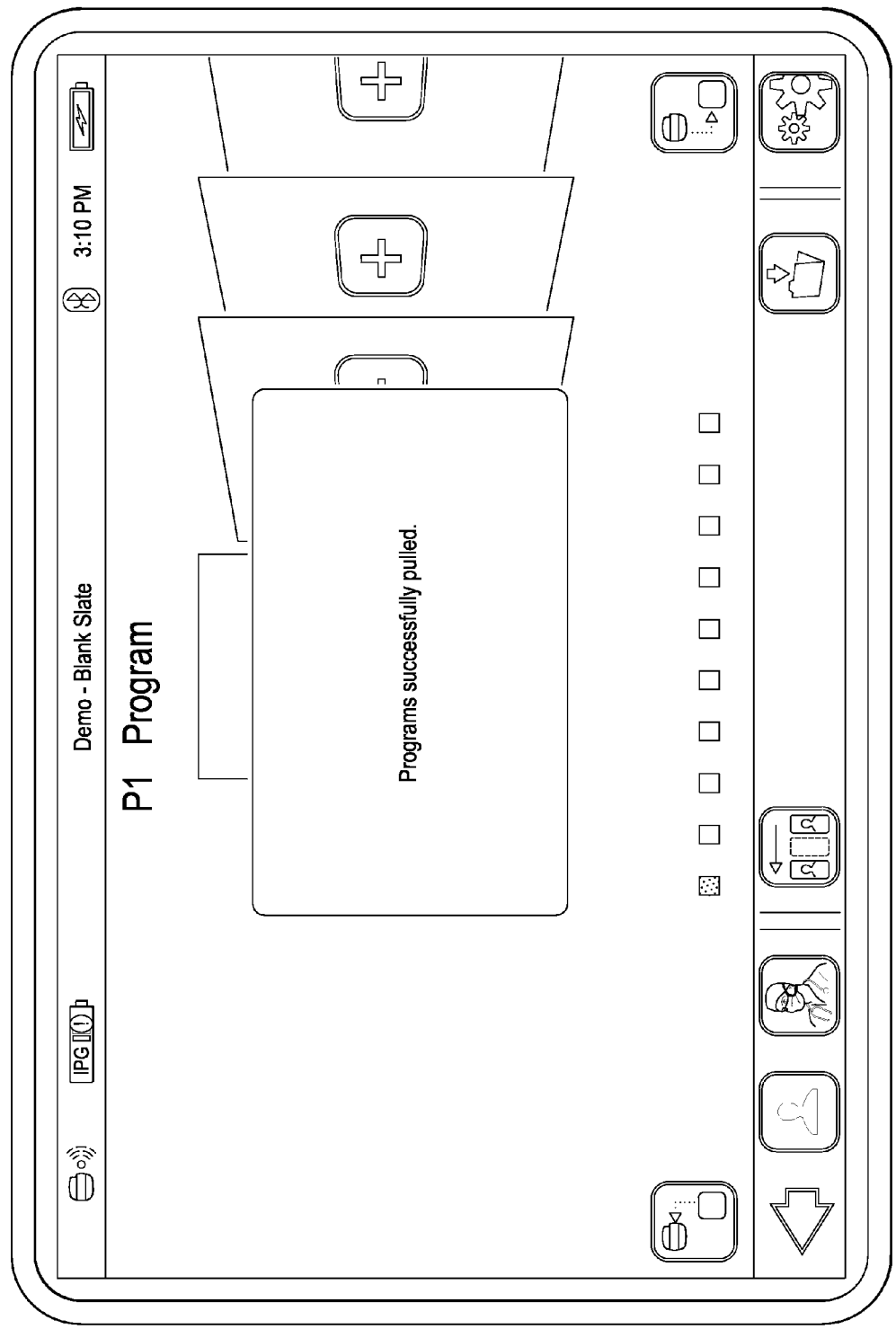
Figure 6:
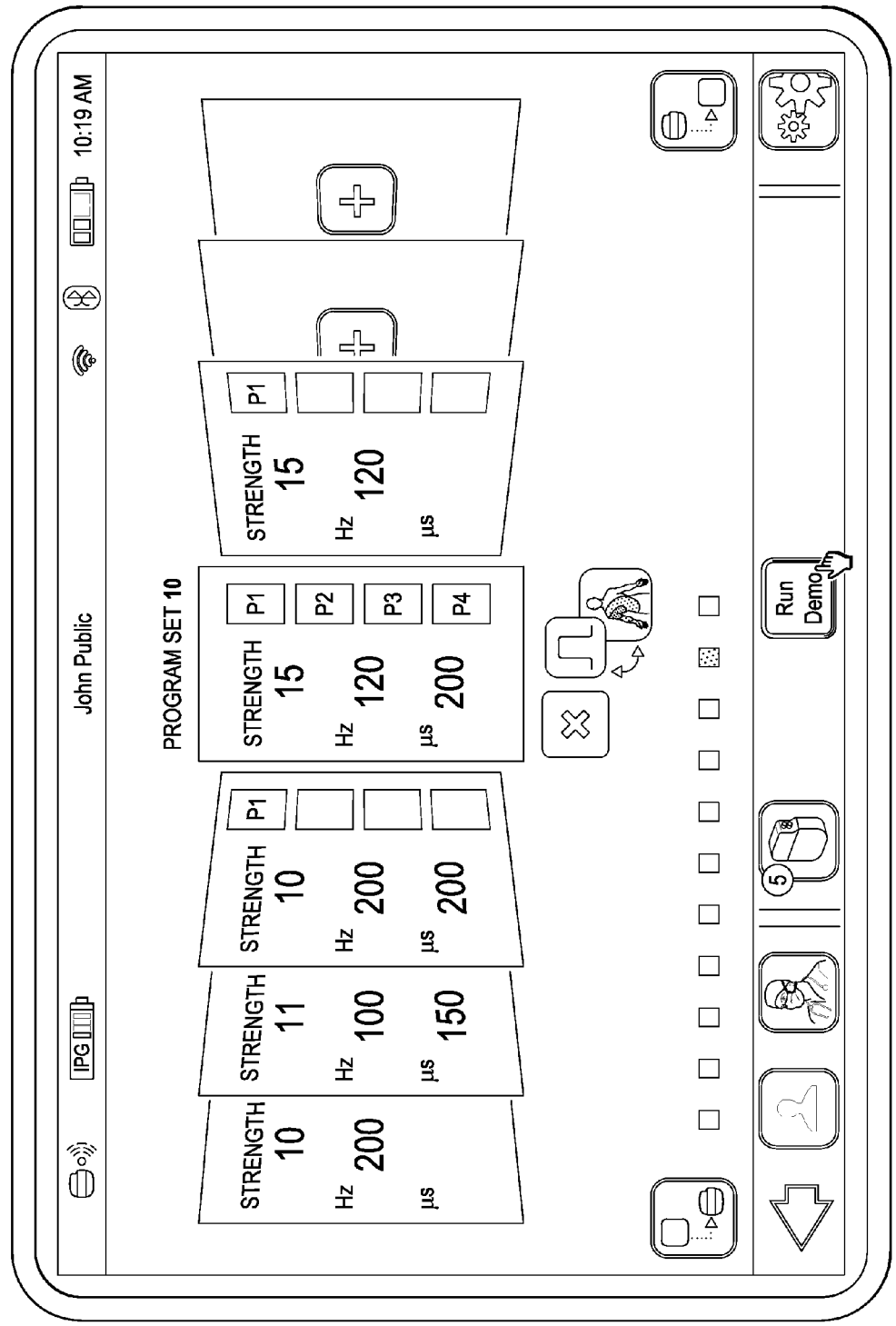

Referring now to FIGS. 5-6, stimulation programs or parameters may be pulled or retrieved from the virtual pulse generator of the pulse generator simulator, just as they can be pulled or retrieved from a real actual pulse generator. The stimulation programs may be represented as one or more virtual icons or cards, as shown in FIG. 6. Additional details for the virtual reality representation of stimulation parameters or programs are described in U.S. patent application Ser. No. 13/601,631, filed on Aug. 31, 2012, entitled "Programming and Virtual Reality Representation of Stimulation Parameter Groups," the disclosure of which is hereby incorporated by reference in its entirety.

Figure 7:
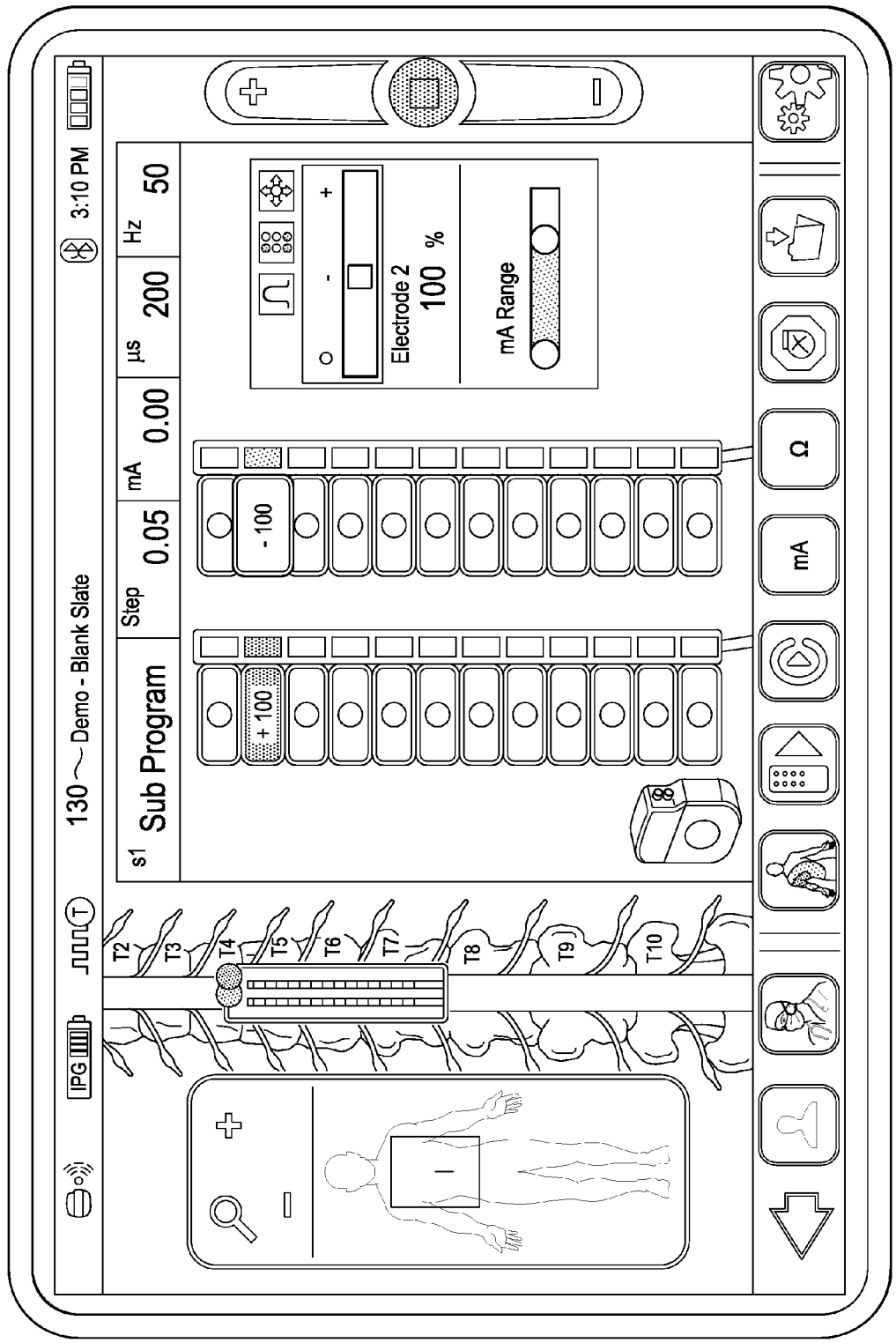

Referring to FIG. 7, the pulse generator simulator allows the user to program stimulation parameters for the virtual pulse generator. This may be done either as the user creates a new stimulation program and enters the new stimulation programming parameters, or as the user modifies the stimulation programming parameters pulled from the virtual pulse generator. As example stimulation programming parameters, the user may set the electrode configuration (anode or cathode) on a lead, or adjust stimulation current amplitude, pulse width, or frequency, etc., for the virtual pulse generator. Once again, the stimulation programming screen shown in FIG. 7 substantially resembles the stimulation programming screen for an actual pulse generator, though the heading 130 still reminds the user that the programming is performed for a virtual pulse generator, not a real one.

When the clinician programmer communicates with the virtual pulse generator, the communication is performed using the same MICS (Medical Implant Communication Service) drivers that it uses to send commands to a physical pulse generator. With the virtual pulse generator in use, however, the clinician programmer does not turn on the MICS radio and does not send commands via MICS. In other words, rather than sending commands to a physical pulse generator through the MICS radio, commands are sent to the pulse generator simulator through the MICS driver instead.

In some embodiments, the pulse generator may save all the programming data (including stimulation programs and/or stimulation parameters) associated with one or more programming sessions of the virtual pulse generator. Such programming data can then be saved, either locally onto a memory storage component of the clinician programmer, or remotely to an electronic database or a cloud network. At a later point in time, when the clinician programmer establishes a connection with a real pulse generator (for example one that is simulated herein by the virtual pulse generator), the clinician programmer may be configured to automatically program that real pulse generator with the saved programming data associated with the virtual pulse generator. By doing so, the user may be spared from having to carry out programming twice for "the same" pulse generator.

Conversely, suppose the clinician programmer had been previously connected to a real actual pulse generator, and the user had already carried out programming for that actual pulse generator, the user may also save the programming data associated with the actual pulse generator. Again, the programming data may be saved locally on a memory storage component of the clinician programmer or remotely to an electronic database or a cloud network. At a later point in time, when the clinician programmer launches the pulse generator simulator (for example one that is designed to simulate the actual pulse generator), the clinician programmer may be configured to automatically program that virtual pulse generator with the saved programming data associated with the actual pulse generator. As is in the case discussed above, the user is spared from having to carry out programming twice for "the same" pulse generator.

Figure 8:
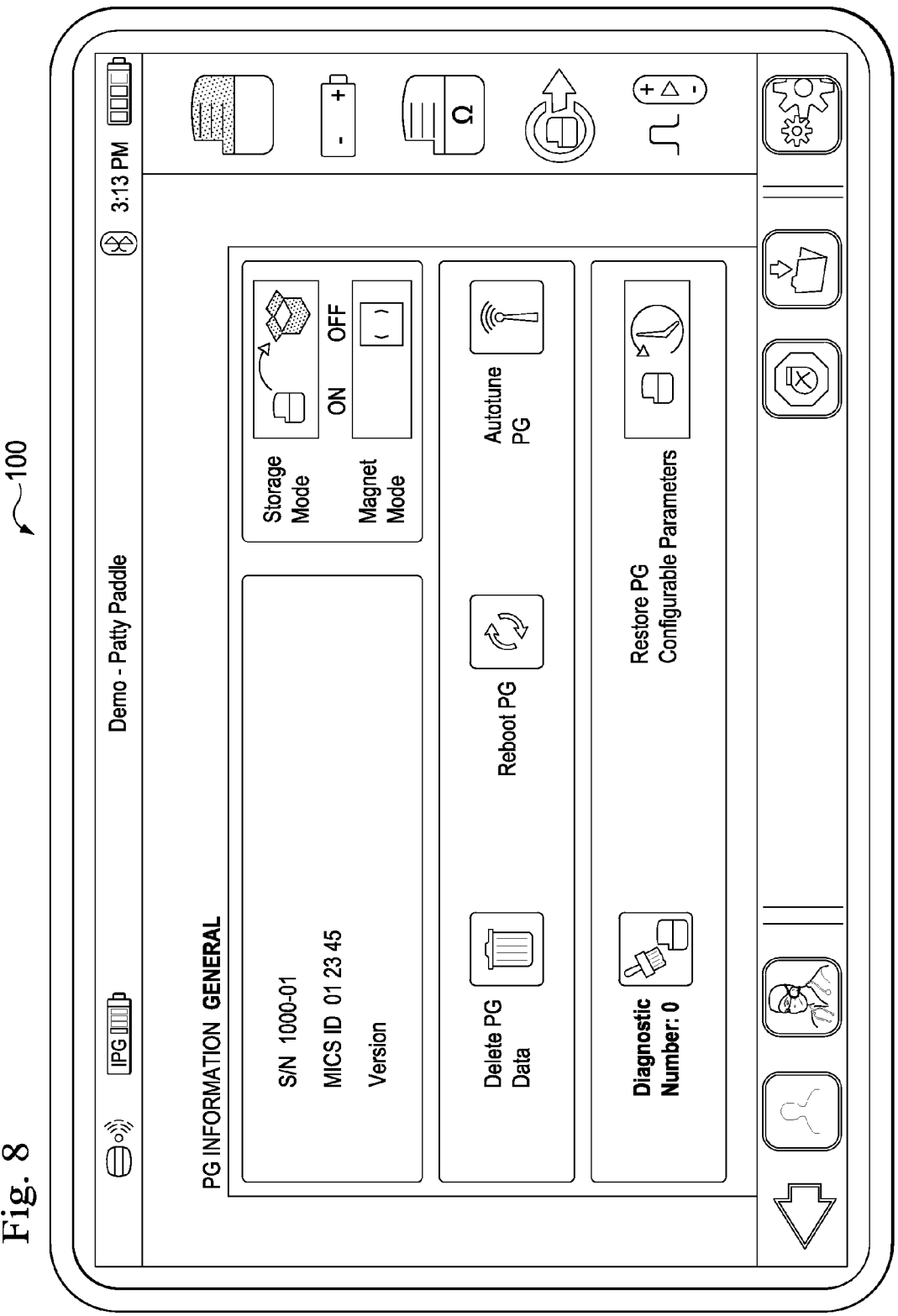

The pulse generator simulator also lets the user retrieve a variety of types of information from the virtual pulse generator or otherwise interact with it in a virtual manner. For example, as shown in FIG. 8, the user may choose to view the information such as a serial number or a MICS ID of the virtual pulse generator. The user may also delete the data on the virtual pulse generator, reboot the virtual pulse generator, auto-tune the virtual pulse generator, restore the virtual pulse generator with configurable parameters, etc. The user may further set a storage mode or a magnet mode for the virtual pulse generator. Again, these are the same types of interactions available to the user had the clinician programmer been engaged with a real pulse generator.

Figure 9:
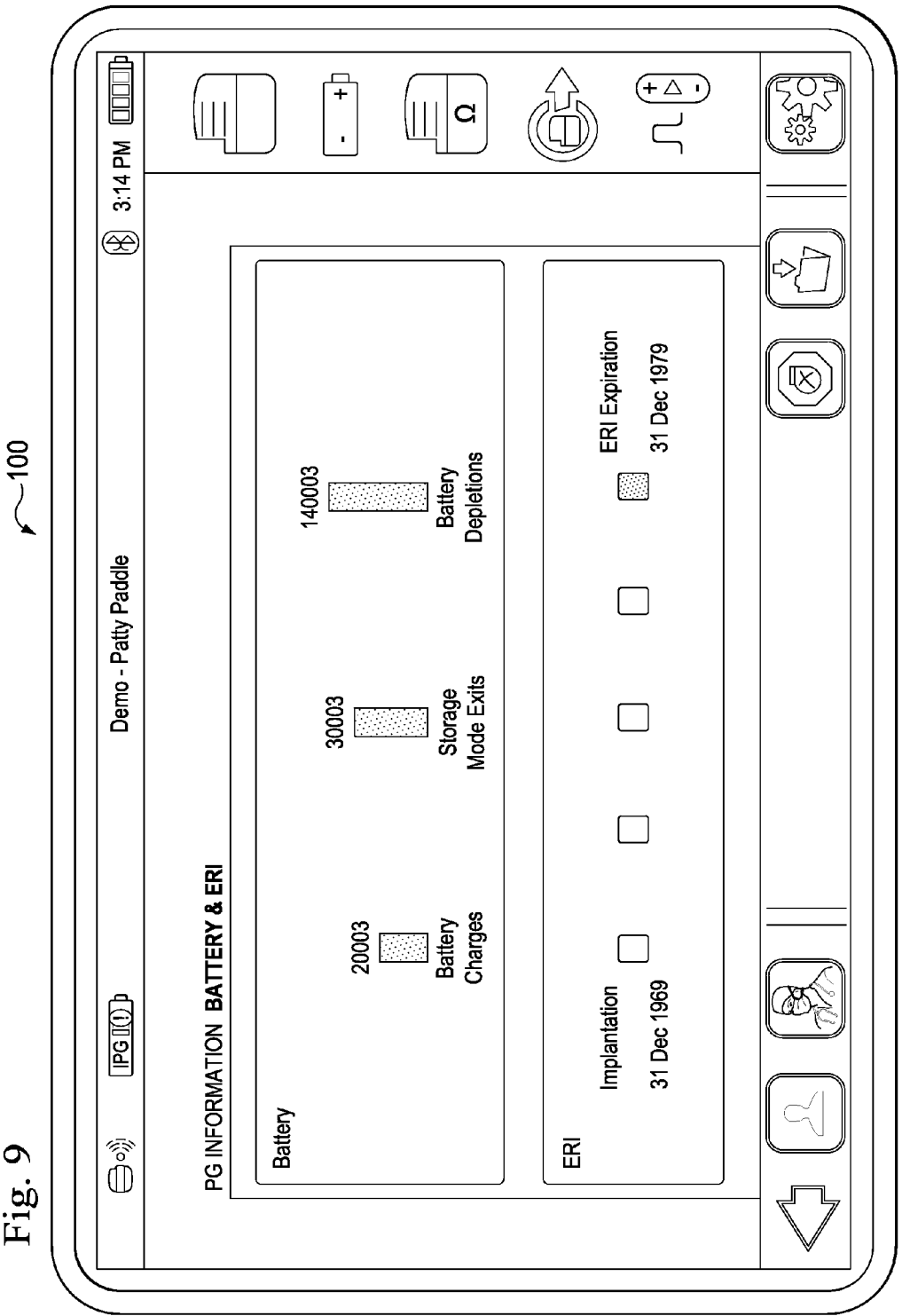
Figure 10:
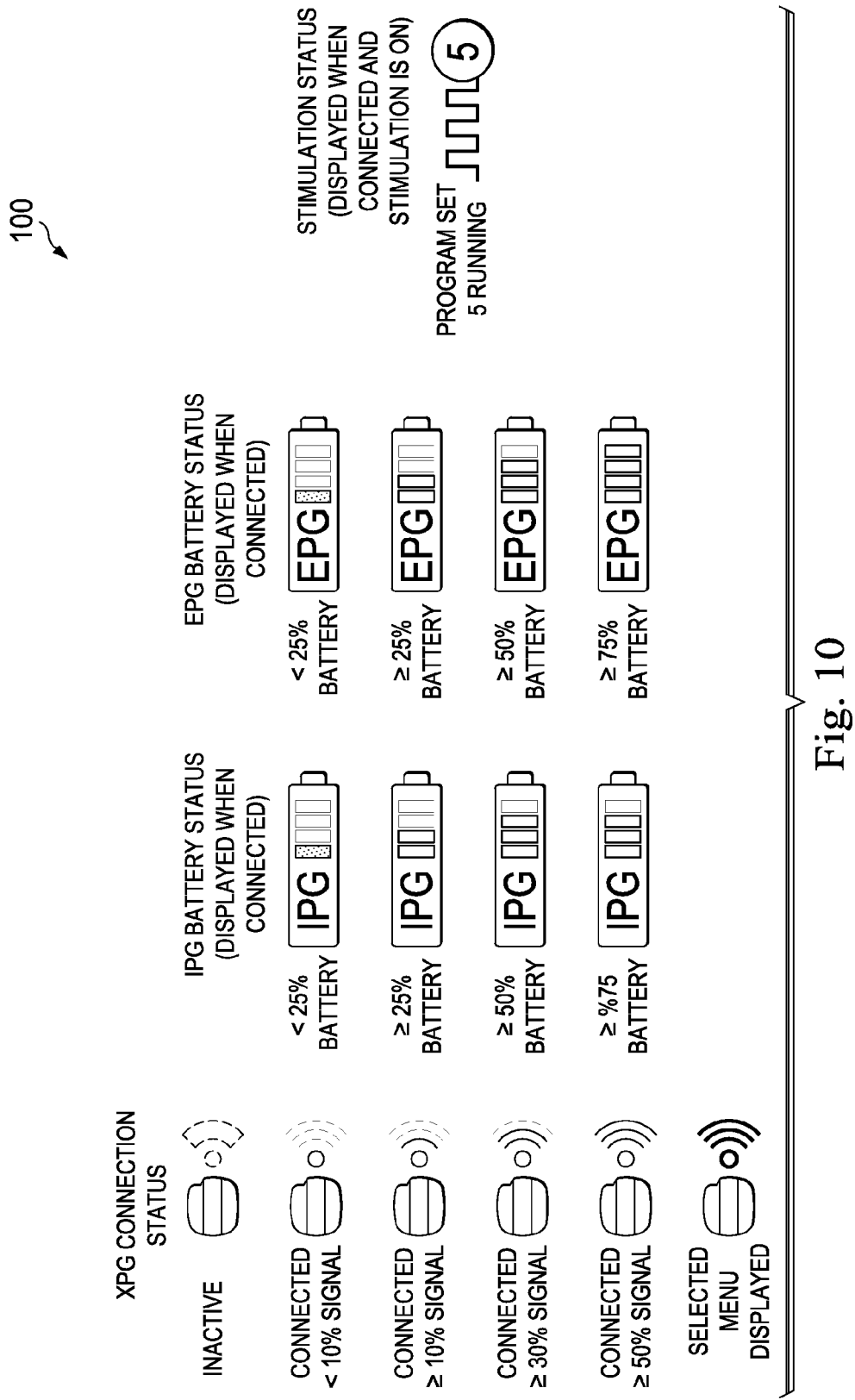

The pulse generator simulator also lets the user review one or more statuses of the virtual pulse generator. For example, as shown in FIG. 9, the user may obtain the battery levels of the virtual pulse generator. The user may also obtain the implantation dates and estimated expiration dates of the virtual pulse generator. The battery levels and implantation and expiration dates may be obtained and displayed the same way for a real physical pulse generator. As additional examples shown in FIG. 10, other types of information related to the virtual pulse generator that can be obtained by the user include: connection status with the virtual pulse generator, battery status of the pulse generator (for both an IPG and an EPG), and stimulation status. These types of information may be displayed as a part of the user interface in the form of small icons or indicators, for example.

Based on the above discussions, it can be seen that a virtual machine on a clinician programmer can fully simulate the features and functionalities of a real actual pulse generator. When users access a portion of the clinician programmer application that normally requires a hardware connection to the actual pulse generator, either the actual pulse generator or the pulse generator simulator can be used. The pulse generator simulator allows users to exercise and/or test the functionality of the clinician programmer (e.g., ability to communicate with an actual pulse generator) without physically generating pulses. If interactions between the pulse generator simulator and the clinician programmer do not have the desired effect, the clinician programmer is unlikely to interact in the desired fashion with the physical pulse generator either. Among other things, this allows the developers of the clinician programmer application to debug and/or improve the application. In addition, the pulse generator simulator also allows the demonstration of results of pulses programmed by the user in the clinician programmer application. Thus, the pulse generator simulator (implemented on a clinician programmer) of the present disclosure allows for easy, intuitive, and accurate testing of the clinician programmer with respect to its predicted interaction with a pulse generator. The pulse generator simulator also allows for quick and hassle-free demonstrations of the clinician programmer's capability to communicate with a pulse generator without actually needing the actual pulse generator.

Figure 11:
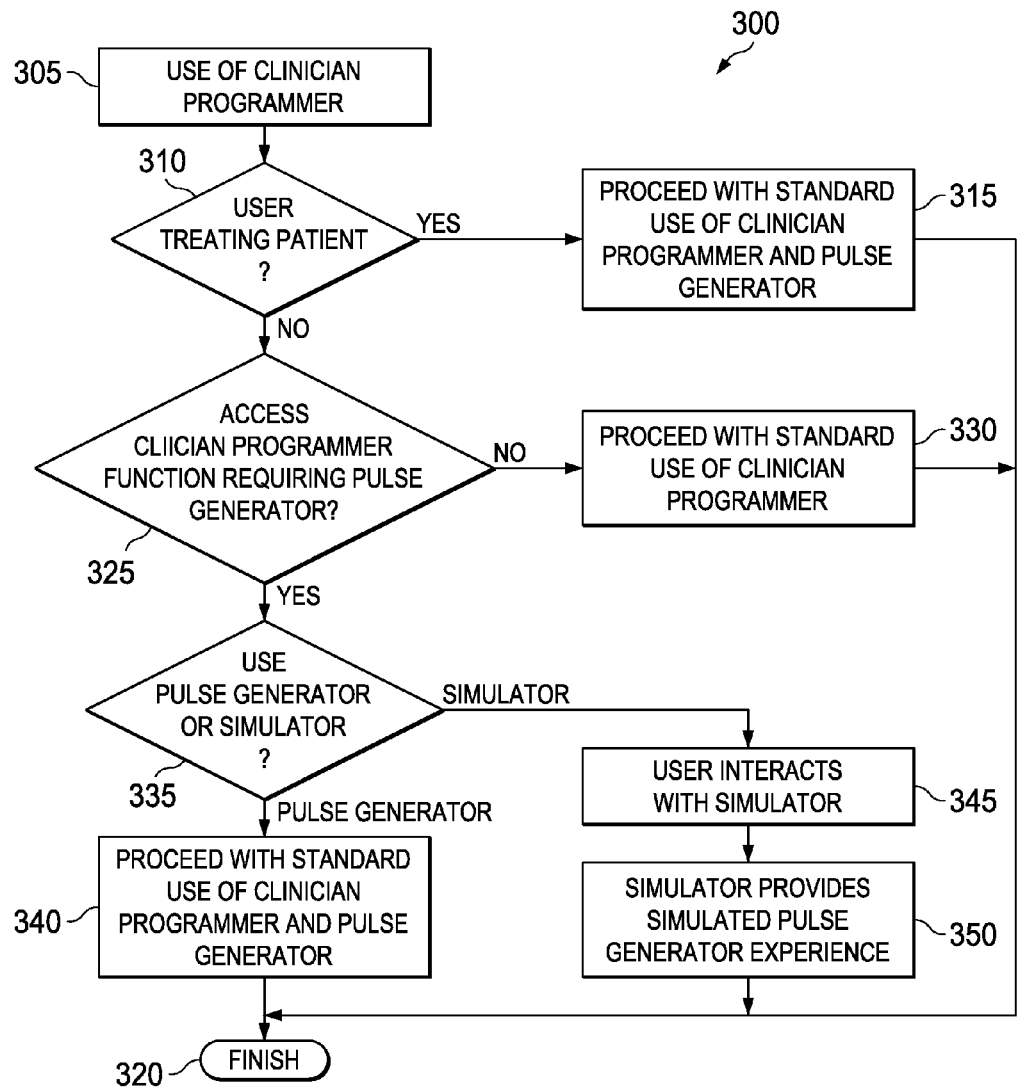
FIGS. 11-13 are simplified flowcharts illustrating a method of simulating a pulse generator according to various aspects of the present disclosure.

FIG. 11 is a simplified flowchart of a method 300 of simulating a pulse generator according to the various aspects of the present disclosure. The method 300 includes a step 305, in which a clinician programmer is used. The method 300 includes a decision step 310 to determine whether the user is trying to treat a patient. If the answer is yes, then the method 300 continues with step 315 to proceed with the standard use of the clinician programmer and pulse generator. The method 300 then finishes at step 320. If the answer from the decision step 310 is no, then the method 300 continues with another step 325 to determine whether the user is trying to access clinician programmer functions that require a pulse generator. If the answer from the decision step 325 is no, then the method 300 continues with a step 330 to proceed with the standard use of the clinician programmer. The method 300 then finishes at step 320. If the answer from the decision step 325 is yes, then the method 300 continues with another decision step 335 to determine whether to use the actual pulse generator or the pulse generator simulator. If the answer from the decision step 335 to use the actual pulse generator, then the method 300 continues with a step 340 to proceed with the standard use of clinician programmer and pulse generator. The method 300 then finishes at step 320. If the answer from the decision step 335 is to use the pulse generator simulator, then the method 300 continues with a step 345, in which the pulse generator simulator is launched, and the user interacts with the pulse generator simulator rather than with the actual pulse generator. The method 300 then continues with a step 350, in which the pulse generator simulator provides a simulated pulse generator experience. The method 300 then finishes at step 320.

It is understood that the method 300 may include additional steps that may be performed before, during, or after the steps 305-350, but these additional steps are not illustrated herein for reasons of simplicity.

Figure 12:
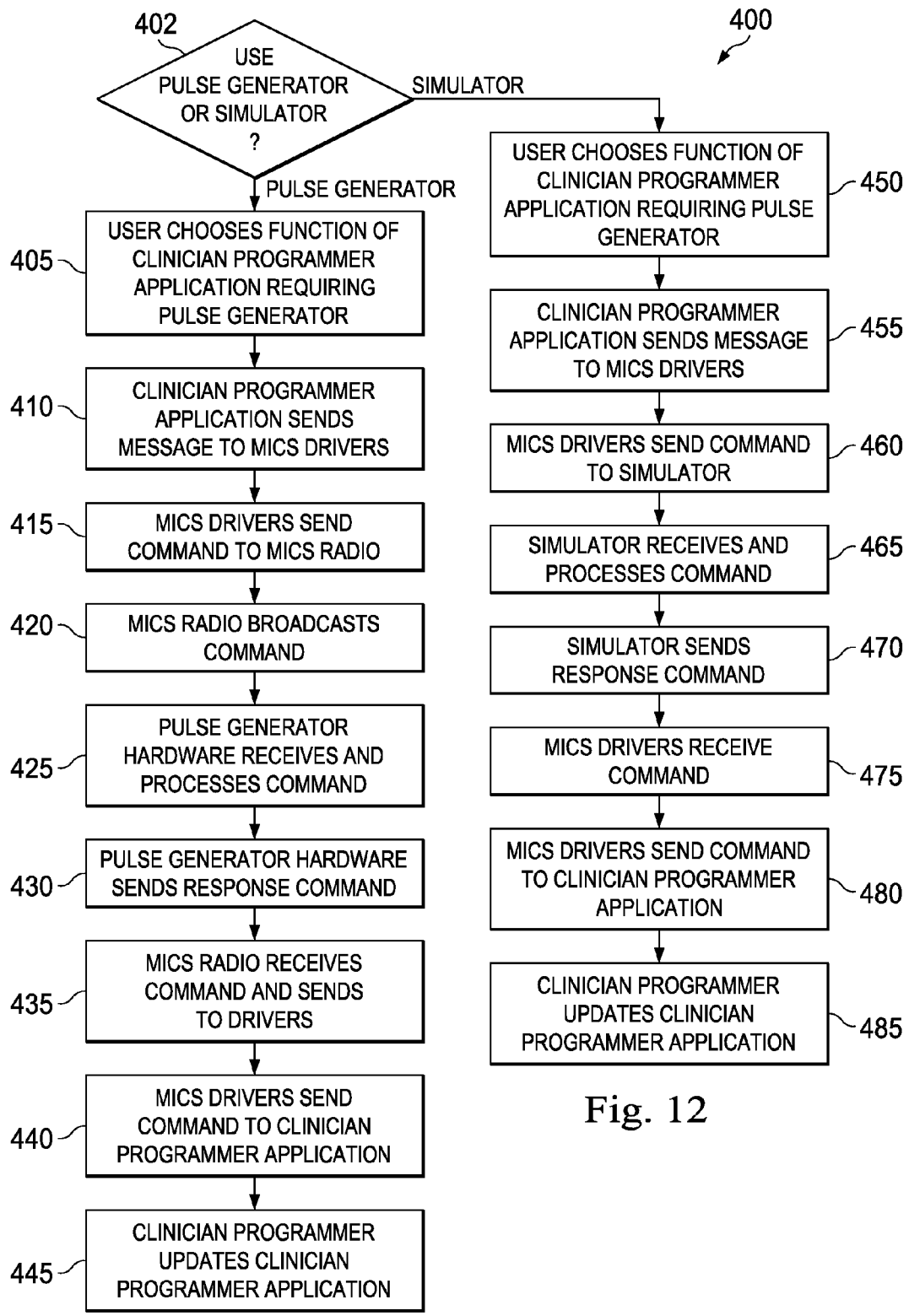

FIG. 12 is a simplified flowchart of a method 400 of using a clinician programmer with either a pulse generator or with a pulse generator simulator according to the various aspects of the present disclosure. The method 400 begins with a decision step 402 to determine whether to use an actual pulse generator or a pulse generator simulator. If the answer from the decision step 402 is to use an actual pulse generator, the method 400 proceeds to a step 405, in which the user chooses the function(s) of the clinician programmer application that require the use of a pulse generator. The method 400 continues with a step 410, in which the clinician programmer application sends messages to MICS drivers. The method 400 continues with a step 415, in which the MICS drivers send commands to the MICS radio. The method 400 continues with a step 420, in which the MICS radio broadcasts command(s). The method 400 continues with a step 425, in which the pulse generator hardware receives and processes the command(s). The method 400 continues with a step 430, in which the pulse generator hardware sends response command. The method 400 continues with a step 435, in which the MICS radio receives command(s) and sends to the drivers. The method 400 continues with a step 440, in which the MICS drivers send command(s) to clinician programmer application. The method 400 continues with a step 445, in which the clinician programmer updates the clinician programmer application.

If the answer from the decision step 402 is to use a pulse generator simulator, then the method 400 proceeds to a step 450, in which the user chooses the function(s) of the clinician programmer application that require the use of a pulse generator. The method 400 continues with a step 455, in which the clinician programmer application sends message to MICS drivers. The method 400 continues with a step 460, in which the MICS drivers send command(s) to the pulse generator simulator. The method 400 continues with a step 465, in which the pulse generator simulator receives and processes the command. The method 400 continues with a step 470, in which the pulse generator simulator sends the response command. The method 400 continues with a step 475, in which the MICS drivers receive the command. The method 400 continues with a step 480, in which the MICS drivers send the command to clinician programmer application. The method 400 continues with a step 485, in which the clinician programmer updates the clinician programmer application.

It is understood that the method 400 may include additional steps that may be performed before, during, or after the steps 402-485, but these additional steps are not illustrated herein for reasons of simplicity.

Figure 13:
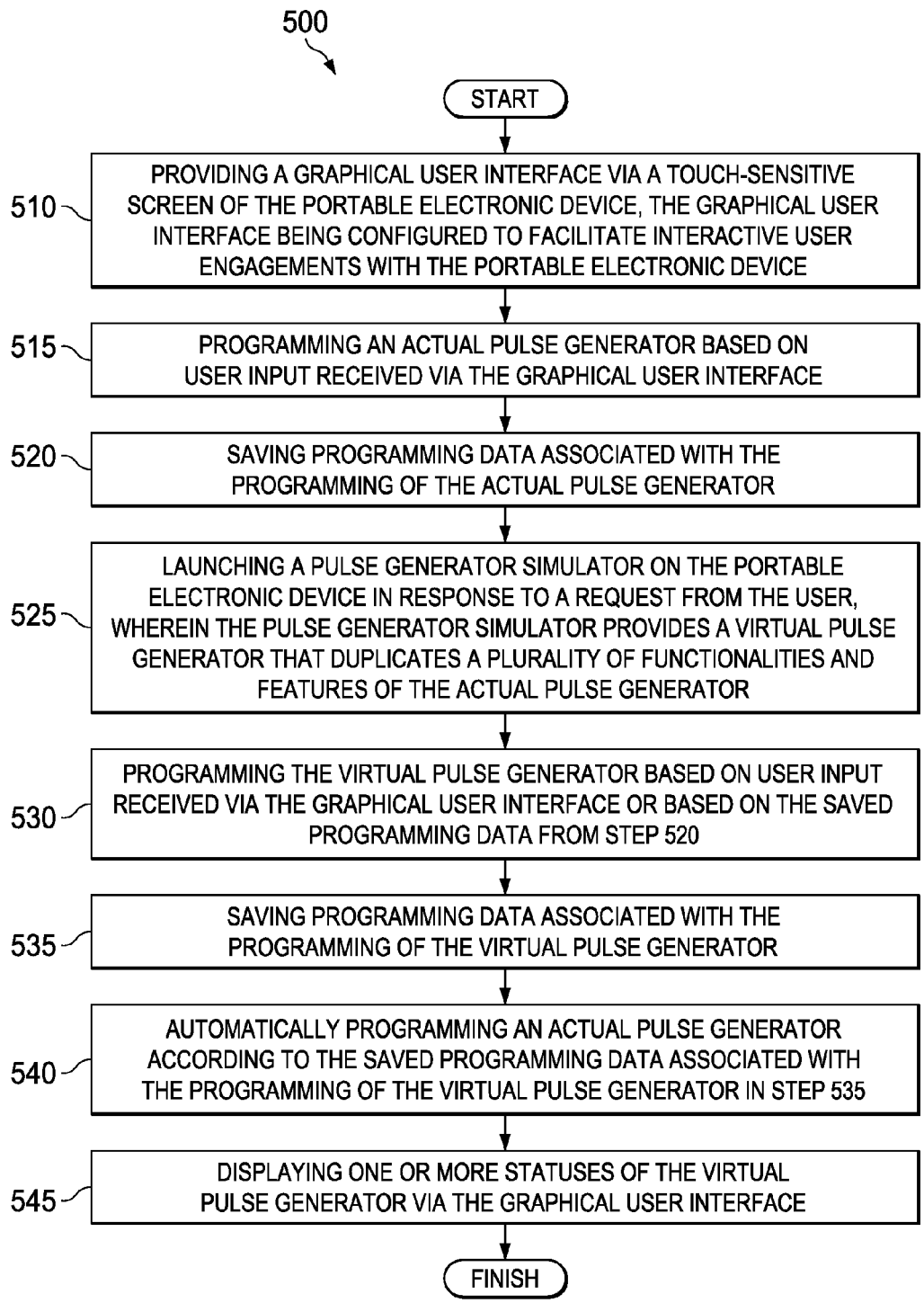

FIG. 13 is a simplified flowchart of a method 500 method of simulating a pulse generator on a portable electronic device according to the various aspects of the present disclosure. The method 500 includes a step 510 of providing a graphical user interface via a touch-sensitive screen of the portable electronic device. The graphical user interface is configured to facilitate interactive user engagements with the portable electronic device. The portable electronic device may be a clinician programmer in some embodiments.

The method 500 includes a step 515 of programming an actual pulse generator based on user input received via the graphical user interface.

The method 500 includes a step 520 of saving programming data associated with the programming of the actual pulse generator.

The method 500 includes a step 525 of launching a pulse generator simulator on the portable electronic device in response to a request from the user. The pulse generator simulator provides a virtual pulse generator that duplicates a plurality of functionalities and features of an actual pulse generator, for example the pulse generator of step 520.

The method 500 includes a step 530 of programming the virtual pulse generator based on user input received via the graphical user interface in some embodiments or based on the saved programming data from step 520 in other embodiments. In embodiments where the saved programming data is used to program the virtual pulse generator, the virtual pulse generator may be automatically programmed without the user having to manually enter the programming data.

The method 500 includes a step 535 of saving programming data associated with the programming of the virtual pulse generator.

The method 500 includes a step 540 of automatically programming an actual pulse generator according to the saved programming data associated with the programming of the virtual pulse generator in step 535. The actual pulse generator being automatically programmed may or may not be the actual pulse generator in step 515.

The method 500 includes a step 545 of displaying one or more statuses of the virtual pulse generator via the graphical user interface. In some embodiments, the one or more statuses include at least one of: a connection status, a battery status, and a stimulation status.

In some embodiments, the steps 525, 530, and 545 are performed without establishing a connection with any actual pulse generators.

It is understood that the method 500 may include additional steps that may be performed before, during, or after the steps 510-545. For example, the method 500 may include the following steps before the pulse generator simulator is launched in step 525: a step of receiving a request from the user to gain access to the portable electronic device; a step of receiving a username and a password from the user; a step of authenticating the user based on the username and password received from the user; a step of displaying an availability of the pulse generator simulator once the user has been authenticated; and a step of thereafter receiving the request from the user to launch the pulse generator simulator. Additional steps may also be performed but are not illustrated herein for reasons of simplicity.

Figure 14:
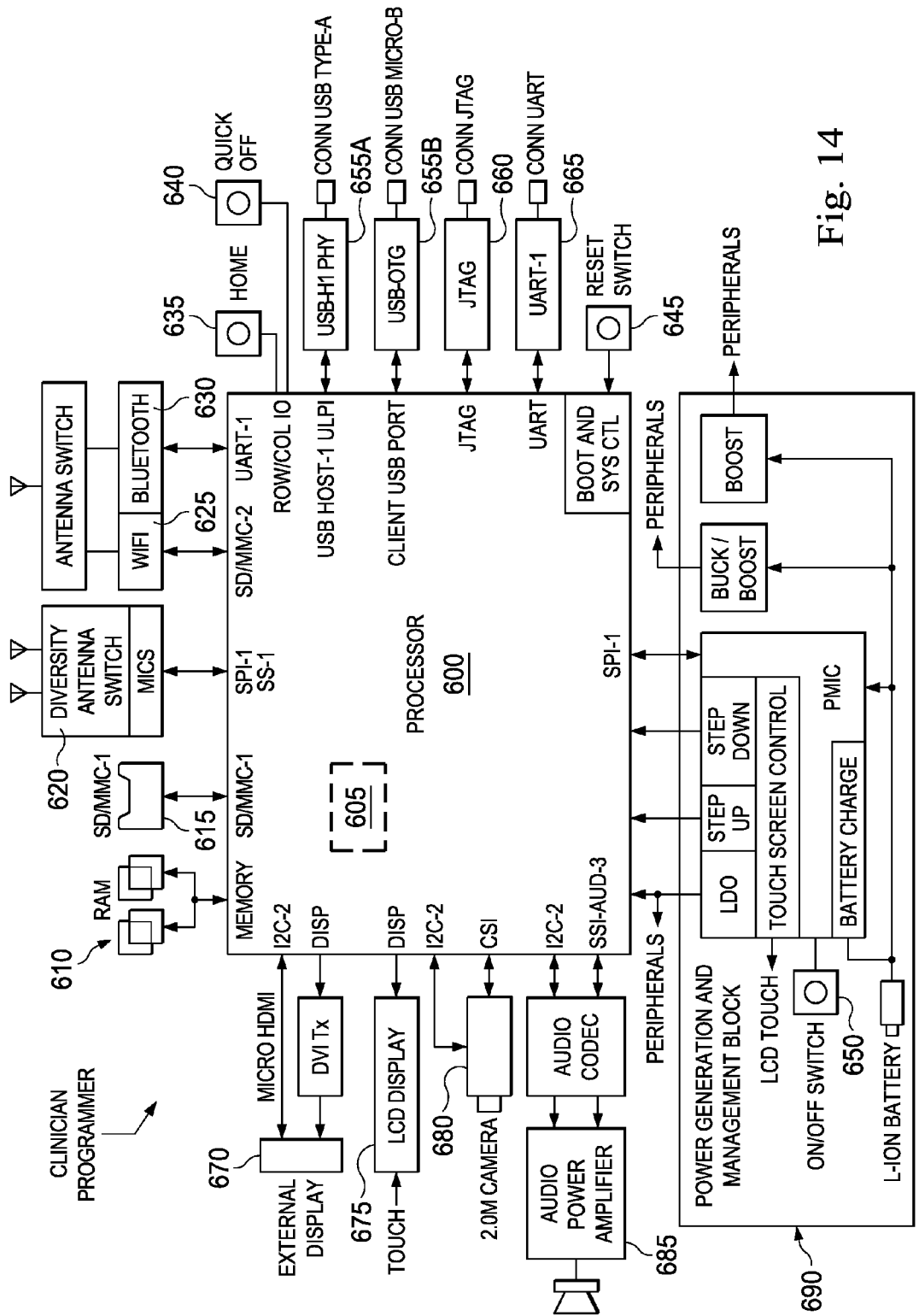
FIG. 14 is a simplified block diagram of an electronic programmer according to various aspects of the present disclosure.

FIG. 14 shows a block diagram of one embodiment of the electronic programmer (CP) discussed herein. For example, the electronic programmer may be a clinician programmer (CP) configured to simulate the pulse generator as discussed above. It is understood, however, that alternative embodiments of the electronic programmer may be used to perform these representations as well.

The CP includes a printed circuit board ("PCB") that is populated with a plurality of electrical and electronic components that provide power, operational control, and protection to the CP. With reference to FIG. 14, the CP includes a processor 600. The processor 600 controls the CP. In one construction, the processor 600 is an applications processor model i.MX515 available from Free scale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX51CEC, Rev. 4" data sheet dated August 2010 and published by Free scale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 14 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 14.

The CP includes multiple bi-directional radio communication capabilities. Specific wireless portions included with the CP are a Medical Implant Communication Service (MICS) bi-directional radio communication portion 620, a Wi-Fi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The Wi-Fi portion 625 and Bluetooth portion 630 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 14.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 14) may also be included for data transfer.

Figure 15:
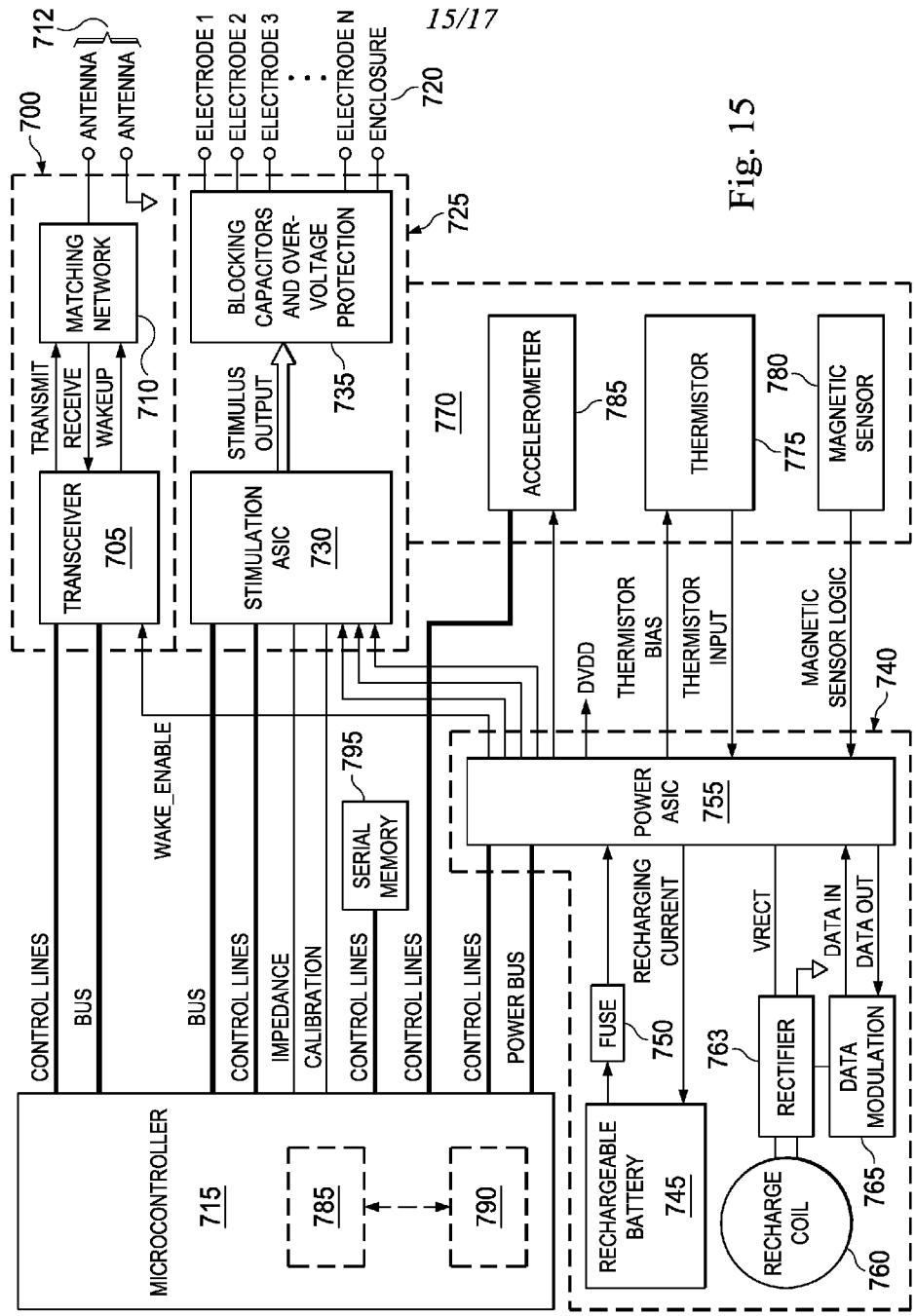
FIG. 15 is a simplified block diagram of an implantable medical device according to various aspects of the present disclosure.

FIG. 15 shows a block diagram of one embodiment of an implantable medical device. In the embodiment shown in FIG. 15, the implantable medical device includes an implantable pulse generator (IPG). The IPG may be an embodiment of the pulse generator that is simulated by the pulse generator simulator application running on the clinician programmer as discussed above with reference to FIGS. 2-13. Referring back to FIG. 15, the IPG includes a printed circuit board ("PCB") that is populated with a plurality of electrical and electronic components that provide power, operational control, and protection to the IPG. With reference to FIG. 15, the IPG includes a communication portion 700 having a transceiver 705, a matching network 710, and antenna 712. The communication portion 700 receives power from a power ASIC (discussed below), and communicates information to/from the microcontroller 715 and a device (e.g., the CP) external to the IPG. For example, the IPG can provide bi-direction radio communication capabilities, including Medical Implant Communication Service (MICS) bi-direction radio communication following the MICS specification.

The IPG provides stimuli to electrodes of an implanted medical electrical lead (not illustrated herein). As shown in FIG. 15, N electrodes are connected to the IPG. In addition, the enclosure or housing 720 of the IPG can act as an electrode. The stimuli are provided by a stimulation portion 225 in response to commands from the microcontroller 215. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, FLASH, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 15 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a signal from the CP.

Referring now to FIG. 16, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above with reference to FIG. 1. For example, the medical devices 810 may be a pulse generator (e.g., the IPG discussed above with reference to FIG. 15), an implantable lead, a charger, or portions thereof. It is understood that each of the medical devices 810 may be a different type of medical device. In other words, the medical devices 810 need not be the same type of medical device.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIG. 14. In other embodiments, the electronic programmer 820A may be a patient programmer or another similar programmer. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage 608 (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 16 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, electronic data may be uploaded from the electronic programmer 820A to the database 900. The data in the database 900 may thereafter be downloaded by any of the other electronic programmers 820B-820N communicatively coupled to it, assuming the user of these programmers has the right login permissions.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

Figure 17A:
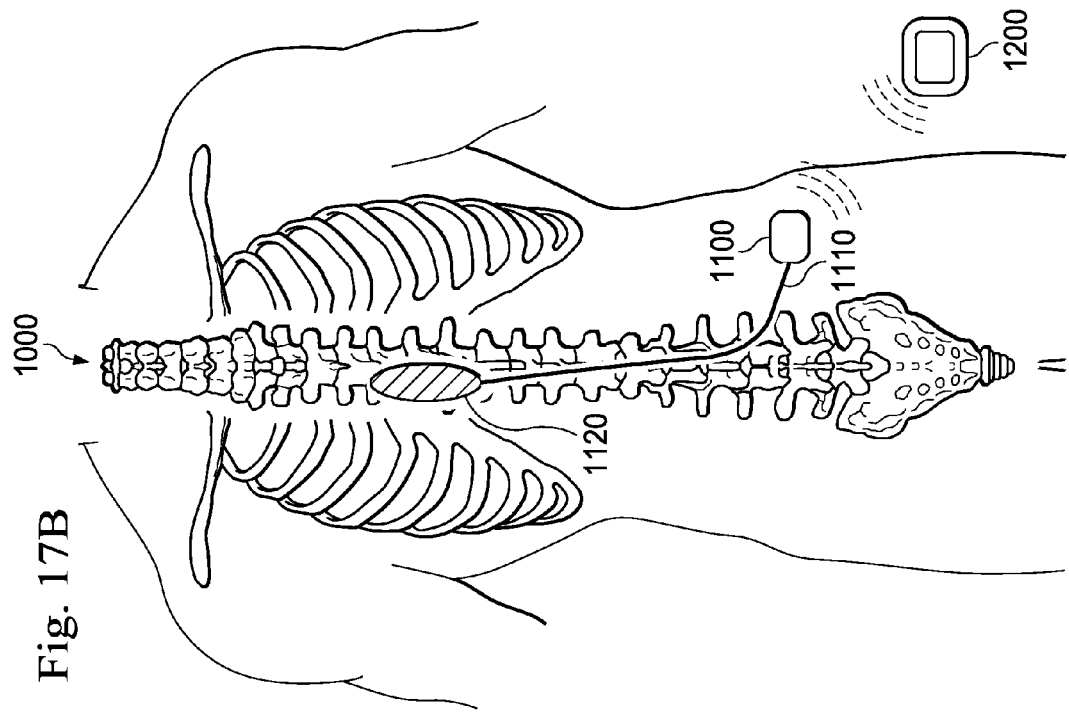
FIGS. 17A and 17B are side and posterior views of a human spine, respectively.
Figure 17B:
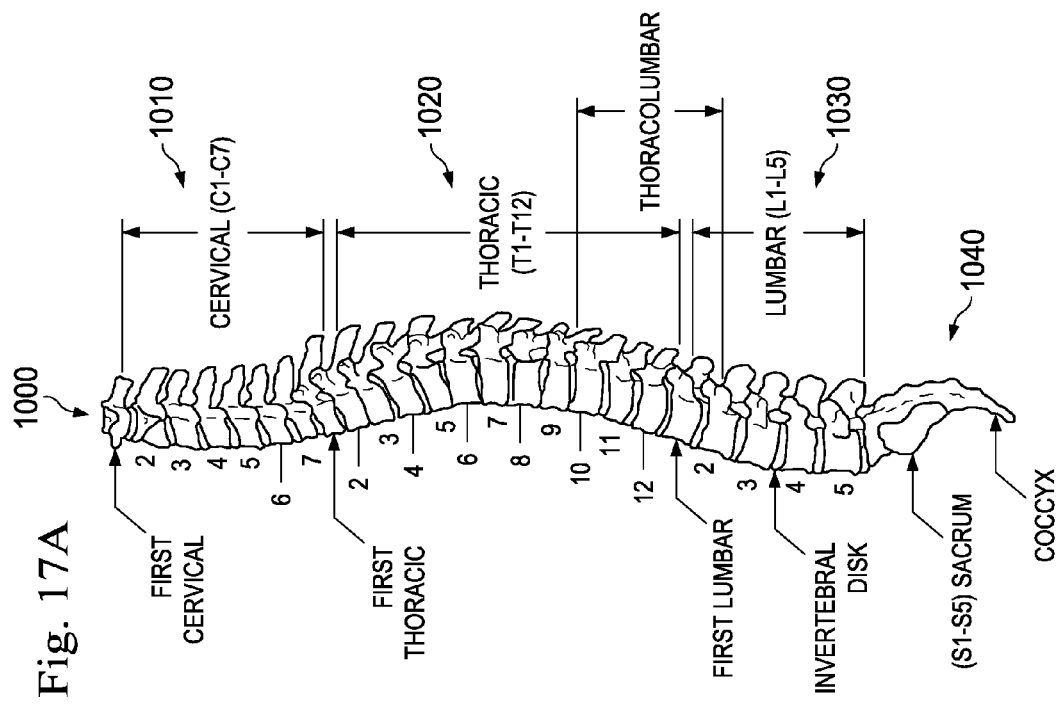

FIG. 17A is a side view of a spine 1000, and FIG. 17B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 17B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 14.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A portable electronic device for simulating a pulse generator, the portable electronic device comprising:
   a touchscreen display configured to receive an input from a user and display an output;
   a memory storage component configured to store programming code; and
   a computer processor configured to execute the programming code to perform the following tasks:
      providing a graphical user interface via the touchscreen display of the portable electronic device;
      launching a pulse generator simulator on the portable electronic device in response to a request from the user, wherein the pulse generator simulator is launched without connecting to an actual pulse generator, and wherein the pulse generator simulator provides a virtual pulse generator that emulates a plurality of functionalities and features of the actual pulse generator;
      programming, without connecting to the actual pulse generator, the virtual pulse generator based on user input received via the graphical user interface;
      displaying one or more statuses of the virtual pulse generator via the graphical user interface, wherein the one or more statuses include at least one of: a connection status, a battery status, and a stimulation status;
      saving programming data associated with the programming of the virtual pulse generator; and
      thereafter establishing a communications link with the actual pulse generator and automatically programming the actual pulse generator according to the saved programming data sent via the communications link;
   wherein the tasks further comprise: before the launching of the pulse generator simulator:
      receiving a request from the user to gain access to the portable electronic device;
      receiving a username and a password from the user;
      authenticating the user based on the username and password received from the user;
      displaying an availability of the pulse generator simulator once the user has been authenticated; and
      thereafter receiving the request from the user to launch the pulse generator simulator.

2. The portable electronic device of claim 1, wherein the tasks further comprise:
   before the launching of the pulse generator simulator, programming the actual pulse generator based on user input received via the graphical user interface; and
   saving programming data associated with the programming of the actual pulse generator, wherein the programming of the virtual pulse generator comprises automatically programming the virtual pulse generator based on the saved programming data associated with the programming of the actual pulse generator.

3. The portable electronic device of claim 1, wherein the portable electronic device is a clinician programmer.

4. The portable electronic device of claim 1, wherein the virtual pulse generator duplicates the plurality of functionalities and features of the actual pulse generator without physically generating pulses.

5. The portable electronic device of claim 1, wherein the actual pulse generator is a hardware device, and wherein the pulse generator simulator is a software program.

6. The portable electronic device of claim 1, wherein the tasks further comprise: simulating an electronic discovery of the virtual pulse generator.

7. A medical system, comprising:
   a pulse generator configured to generate electrical pulses for stimulating target nerve tissues of a patient; and
   a portable electronic device configured to simulate the pulse generator, wherein the portable electronic device includes a non-transitory, tangible machine-readable storage medium storing executable instructions that when executed electronically by one or more processors, perform the following operations:
      providing a graphical user interface via a touch-sensitive screen of the portable electronic device, the graphical user interface being configured to facilitate interactive user engagements with the portable electronic device;
      launching a pulse generator simulator on the portable electronic device in response to a request from the user, wherein the pulse generator simulator is launched without connecting to an actual pulse generator, and wherein the pulse generator simulator provides a virtual pulse generator that emulates a plurality of functionalities and features of the actual pulse generator;
      programming, without connecting to the actual pulse generator, the virtual pulse generator based on user input received via the graphical user interface;
      displaying one or more statuses of the virtual pulse generator via the graphical user interface, wherein the one or more statuses include at least one of: a connection status, a battery status, and a stimulation status;
      saving programming data associated with the programming of the virtual pulse generator; and
      thereafter establishing a communications link with the actual pulse generator and automatically programming the actual pulse generator according to the saved programming data sent via the communications link;
wherein the operations further comprise: before the launching of the pulse generator simulator:
receiving a request from the user to gain access to the portable electronic device;
receiving a username and a password from the user;
authenticating the user based on the username and password received from the user;
displaying an availability of the pulse generator simulator once the user has been authenticated; and
thereafter receiving the request from the user to launch the pulse generator simulator.

8. The medical system of claim 7, further comprising: a lead configured for coupling with the pulse generator and for delivering the electrical pulses to the target nerve tissues of the patient.

9. The medical system of claim 7, wherein the operations further comprise:
before the launching of the pulse generator simulator, programming the actual pulse generator based on user input received via the graphical user interface; and
saving programming data associated with the programming of the actual pulse generator, wherein the programming of the virtual pulse generator comprises automatically programming the virtual pulse generator based on the saved programming data associated with the programming of the actual pulse generator.

10. The medical system of claim 7, wherein the portable electronic device is a clinician programmer.

11. The medical system of claim 7, wherein the virtual pulse generator duplicates the plurality of functionalities and features of the actual pulse generator without physically generating pulses.

12. The medical system of claim 7, wherein the actual pulse generator is a hardware device, and wherein the pulse generator simulator is a software program.

13. The medical system of claim 7, wherein the operations further comprise: simulating an electronic discovery of the virtual pulse generator.

14. A method of simulating a pulse generator on a portable electronic device, the method comprising:
providing a graphical user interface via a touch-sensitive screen of the portable electronic device, the graphical user interface being configured to facilitate interactive user engagements with the portable electronic device;
launching a pulse generator simulator on the portable electronic device in response to a request from the user, wherein the pulse generator simulator is launched without connecting to an actual pulse generator, and wherein the pulse generator simulator provides a virtual pulse generator that emulates a plurality of functionalities and features of the actual pulse generator;
programming, without connecting to the actual pulse generator, the virtual pulse generator based on user input received via the graphical user interface;
displaying one or more statuses of the virtual pulse generator via the graphical user interface, wherein the one or more statuses include at least one of: a connection status, a battery status, and a stimulation status;
saving programming data associated with the programming of the virtual pulse generator; and
thereafter establishing a communications link with the actual pulse generator and automatically programming the actual pulse generator according to the saved programming data sent via the communications link;
wherein the method further comprising: before the launching of the pulse generator simulator:
receiving a request from the user to gain access to the portable electronic device;
receiving a username and a password from the user;
authenticating the user based on the username and password received from the user;
displaying an availability of the pulse generator simulator once the user has been authenticated; and
thereafter receiving the request from the user to launch the pulse generator simulator.

15. The method of claim 14, further comprising:
before the launching of the pulse generator simulator, programming the actual pulse generator based on user input received via the graphical user interface; and
saving programming data associated with the programming of the actual pulse generator, wherein the programming of the virtual pulse generator comprises automatically programming the virtual pulse generator based on the saved programming data associated with the programming of the actual pulse generator.

16. The method of claim 14, wherein the portable electronic device is a clinician programmer.

17. The method of claim 14, wherein the virtual pulse generator duplicates the plurality of functionalities and features of the actual pulse generator without physically generating pulses.

18. The method of claim 14, wherein the actual pulse generator is a hardware device, and wherein the pulse generator simulator is a software program.

19. The method of claim 14, further comprising: simulating an electronic discovery of the virtual pulse generator.

20. An electronic apparatus for simulating a pulse generator, the electronic apparatus comprising:
user interface means for communicating with a user;
memory storage means for storing executable programming instructions; and
computer processor means for executing the programming instructions to perform the following steps:
launching a pulse generator simulator in response to a request from the user, wherein the pulse generator simulator is launched without connecting to an actual pulse generator, and wherein the pulse generator simulator provides a virtual pulse generator that emulates a plurality of functionalities and features of the actual pulse generator that is programmable to deliver electrical stimulation therapy for a patient;
programming, without connecting to the actual pulse generator, the virtual pulse generator based on user input received via the user interface means;
displaying one or more statuses of the virtual pulse generator via the user interface means, wherein the one or more statuses include at least one of: a connection status, a battery status, and a stimulation status;
saving programming data associated with the programming of the virtual pulse generator; and
thereafter establishing a communications link with the actual pulse generator and automatically programming the actual pulse generator according to the saved programming data;
wherein the steps further comprise: before the launching of the pulse generator simulator:
receiving a request from the user to gain access to the electronic apparatus;
receiving a username and a password from the user;

authenticating the user based on the username and password received from the user;

displaying an availability of the pulse generator simulator once the user has been authenticated; and thereafter receiving the request from the user to launch the pulse generator simulator.

21. The electronic apparatus of claim 20, wherein the steps further comprise:

before the launching of the pulse generator simulator, programming the actual pulse generator based on user input received via the user interface means; and saving programming data associated with the programming of the actual pulse generator, wherein the programming of the virtual pulse generator comprises automatically programming the virtual pulse generator based on the saved programming data associated with the programming of the actual pulse generator.

22. The electronic apparatus of claim 20, wherein the virtual pulse generator duplicates the plurality of functionalities and features of the actual pulse generator without physically generating pulses.

23. The electronic apparatus of claim 20, wherein the actual pulse generator is a hardware device, and wherein the pulse generator simulator is a software program.

24. The electronic apparatus of claim 20, wherein the steps further comprise: simulating an electronic discovery of the virtual pulse generator.

\* \* \* \* \*